(12) United States Patent
Arai

(10) Patent No.: US 8,753,263 B2
(45) Date of Patent: Jun. 17, 2014

(54) INSERTION APPARATUS

(71) Applicant: Olympus Medical Systems Corp., Tokyo (JP)

(72) Inventor: Keiichi Arai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/766,244

(22) Filed: Feb. 13, 2013

(65) Prior Publication Data

US 2013/0205937 A1 Aug. 15, 2013

Related U.S. Application Data

(63) Continuation of application No. PCT/JP2012/064899, filed on Jun. 11, 2012.

(30) Foreign Application Priority Data

Jul. 15, 2011 (JP) ................................. 2011-157093

(51) Int. Cl.
*A61B 1/00* (2006.01)

(52) U.S. Cl.
USPC ........................... 600/144; 600/146; 600/148

(58) Field of Classification Search
CPC .... A61B 1/005; A61B 1/0051; A61B 1/0052; A61B 1/0055; A61B 1/0057
USPC .................................. 600/141, 144, 146, 148
See application file for complete search history.

(56) References Cited

U.S. PATENT DOCUMENTS

| 4,762,119 | A | * | 8/1988 | Allred et al. ................... 600/149 |
| 5,174,277 | A | * | 12/1992 | Matsumaru ................... 600/142 |
| 5,472,017 | A | * | 12/1995 | Kovalcheck ................... 138/103 |
| 5,507,717 | A | * | 4/1996 | Kura et al. ..................... 600/146 |
| 5,569,157 | A | * | 10/1996 | Nakazawa et al. ............ 600/107 |

(Continued)

FOREIGN PATENT DOCUMENTS

| EP | 2 103 247 A1 | 9/2009 |
| JP | A-09-294710 | 11/1997 |

(Continued)

OTHER PUBLICATIONS

Sep. 11, 2012 International Search Report issued in International Application No. PCT/JP2012/064899 (with translation).

(Continued)

*Primary Examiner* — Anhtuan T Nguyen
*Assistant Examiner* — Jae Woo
(74) *Attorney, Agent, or Firm* — Oliff PLC

(57) ABSTRACT

An insertion apparatus includes a moving unit moving between a first movement position in a state that a motion portion performs a motion and a second movement position in a state that the motion of the motion portion is regulated. A link unit oh the insertion apparatus includes a coupling portion which couples a first link with a second link in a state that the first link and the second link form a substantially V-like shape having a link coupling position as an apex when the moving unit is placed at the first movement position and in a state that the first link and the second link form a substantially linear shape that does not bend at the link coupling position when the moving unit is placed at the second movement position.

12 Claims, 18 Drawing Sheets

(56) References Cited

U.S. PATENT DOCUMENTS

| | | | |
|---|---|---|---|
| 5,667,476 A * | 9/1997 | Frassica et al. | 600/149 |
| 5,810,715 A * | 9/1998 | Moriyama | 600/144 |
| 5,833,616 A * | 11/1998 | Gruner et al. | 600/462 |
| 5,842,993 A * | 12/1998 | Eichelberger et al. | 600/462 |
| 5,976,074 A | 11/1999 | Moriyama | |
| 6,638,213 B2 * | 10/2003 | Ogura et al. | 600/148 |
| 6,743,239 B1 * | 6/2004 | Kuehn et al. | 606/139 |
| 6,783,491 B2 * | 8/2004 | Saadat et al. | 600/114 |
| 6,827,683 B2 * | 12/2004 | Otawara | 600/123 |
| 6,942,613 B2 * | 9/2005 | Ewers et al. | 600/114 |
| 7,087,010 B2 * | 8/2006 | Ootawara et al. | 600/104 |
| 7,736,303 B2 * | 6/2010 | Miyagi et al. | 600/146 |
| 7,837,615 B2 * | 11/2010 | Le et al. | 600/149 |
| 8,308,634 B2 * | 11/2012 | Torii | 600/149 |
| 8,366,606 B2 * | 2/2013 | Watanabe et al. | 600/144 |
| 2003/0233025 A1 | 12/2003 | Saadat et al. | |
| 2003/0233026 A1 | 12/2003 | Saadat et al. | |
| 2003/0233027 A1 | 12/2003 | Ewers et al. | |
| 2003/0233056 A1 | 12/2003 | Saadat et al. | |
| 2003/0233057 A1 | 12/2003 | Saadat et al. | |
| 2003/0233058 A1 | 12/2003 | Ewers et al. | |
| 2003/0233066 A1 | 12/2003 | Ewers et al. | |
| 2004/0138529 A1 * | 7/2004 | Wiltshire et al. | 600/144 |
| 2004/0186350 A1 * | 9/2004 | Brenneman et al. | 600/146 |
| 2005/0065404 A1 | 3/2005 | Moriyama | |
| 2006/0178562 A1 * | 8/2006 | Saadat et al. | 600/142 |
| 2007/0251976 A1 * | 11/2007 | Sonnenschein et al. | 227/175.1 |
| 2008/0051655 A1 * | 2/2008 | Sato et al. | 600/439 |
| 2009/0287054 A1 * | 11/2009 | Dejima et al. | 600/146 |
| 2010/0168519 A1 * | 7/2010 | Matsuo | 600/139 |
| 2011/0166422 A1 * | 7/2011 | Ross et al. | 600/204 |
| 2011/0282153 A1 * | 11/2011 | Ueki | 600/149 |
| 2011/0288375 A1 * | 11/2011 | Ouchi | 600/114 |
| 2013/0038930 A1 * | 2/2013 | Vent | 359/362 |
| 2013/0096384 A1 * | 4/2013 | Arai | 600/144 |
| 2013/0205937 A1 * | 8/2013 | Arai | 74/527 |

FOREIGN PATENT DOCUMENTS

| | | |
|---|---|---|
| JP | A-2004-321492 | 11/2004 |
| JP | A-2006-512935 | 4/2006 |
| JP | A-2008-099743 | 5/2008 |

OTHER PUBLICATIONS

Feb. 17, 2014 Search Report issued in European Patent Application No. 12814137.1.

* cited by examiner

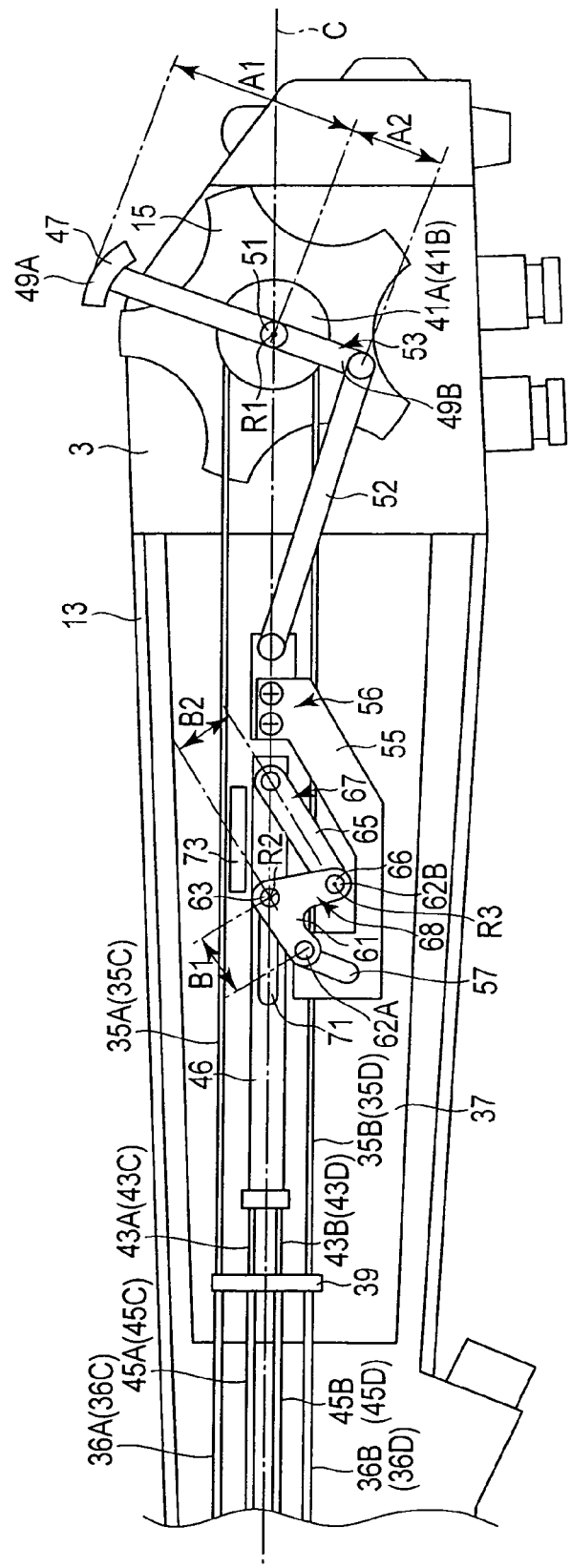
F I G. 6

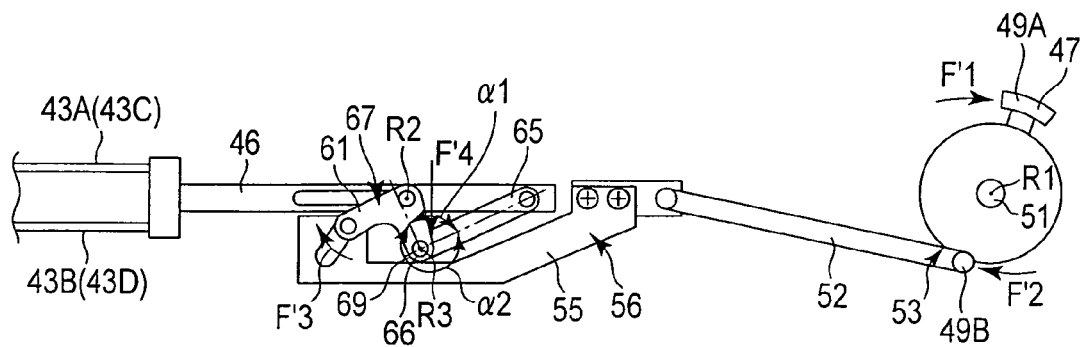
F I G. 9
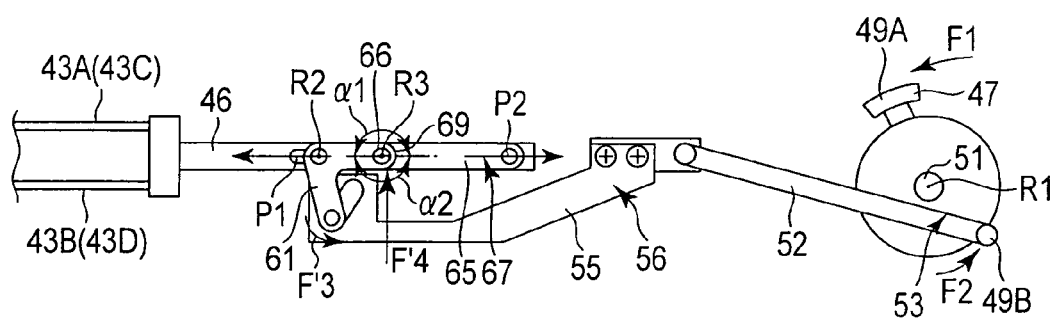
F I G. 10

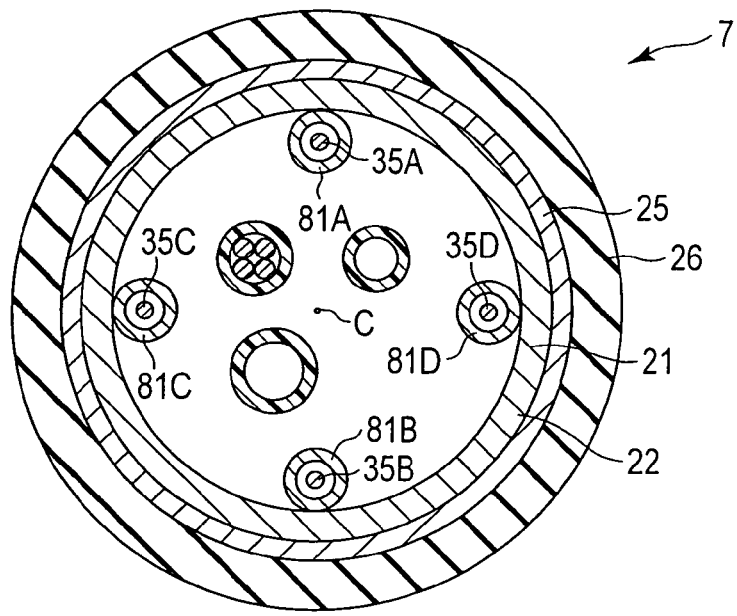
F I G. 12
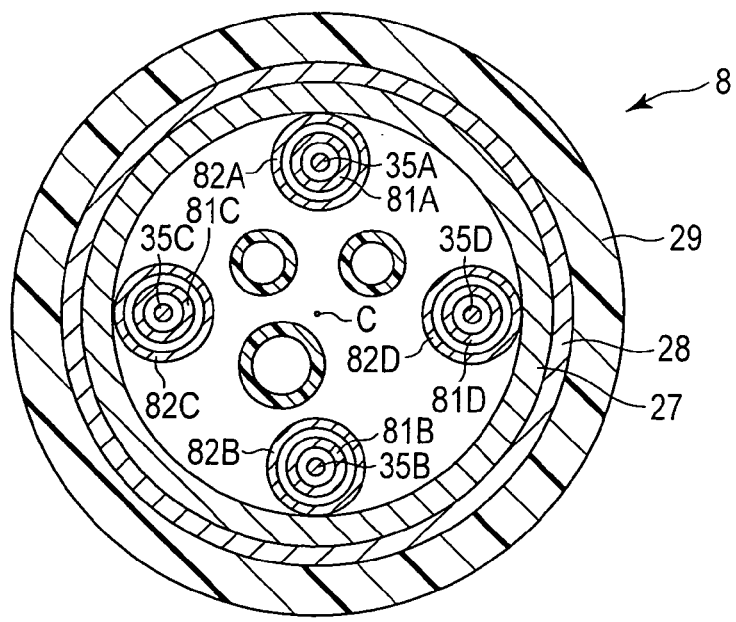
F I G. 13

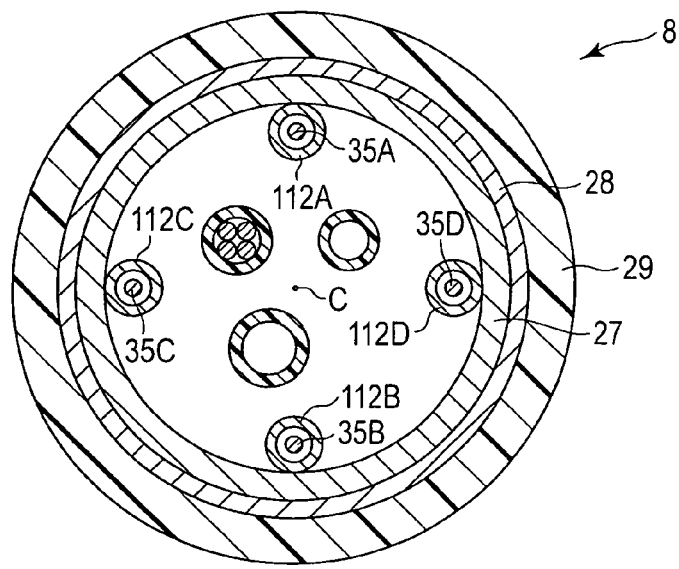
F I G. 21
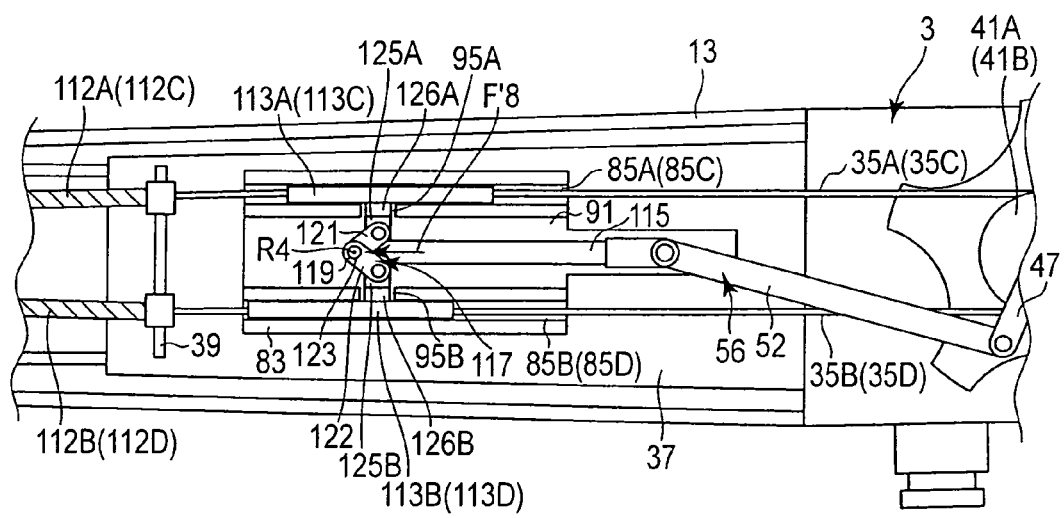
F I G. 22

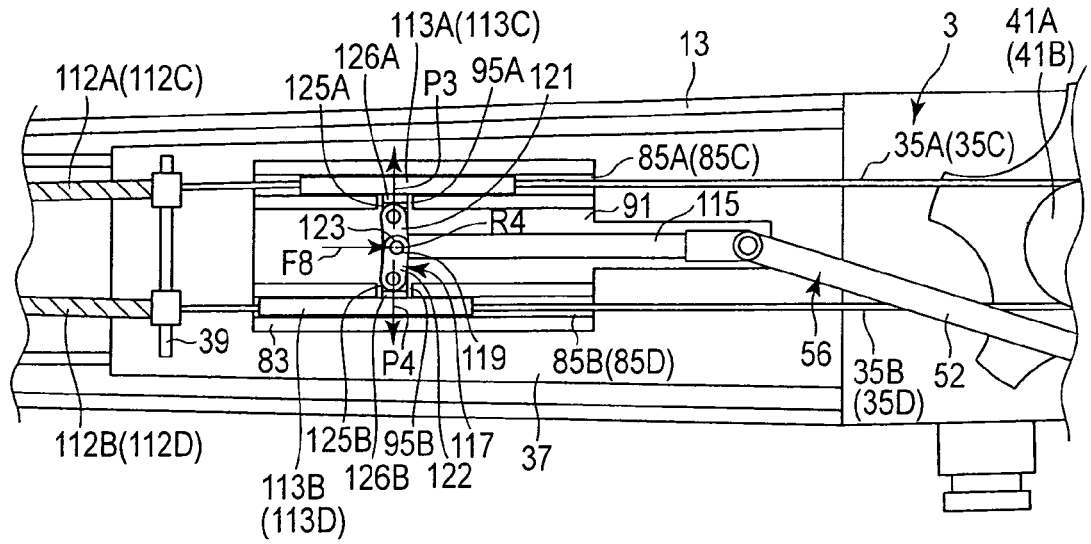
F I G. 23
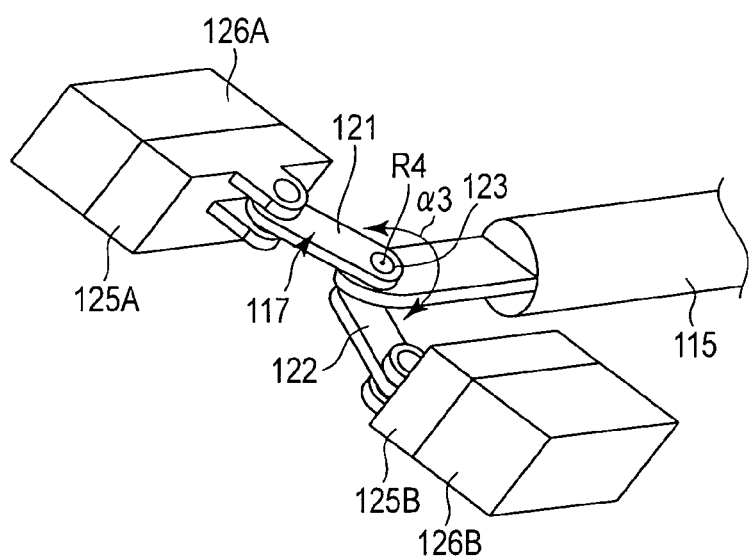
F I G. 24

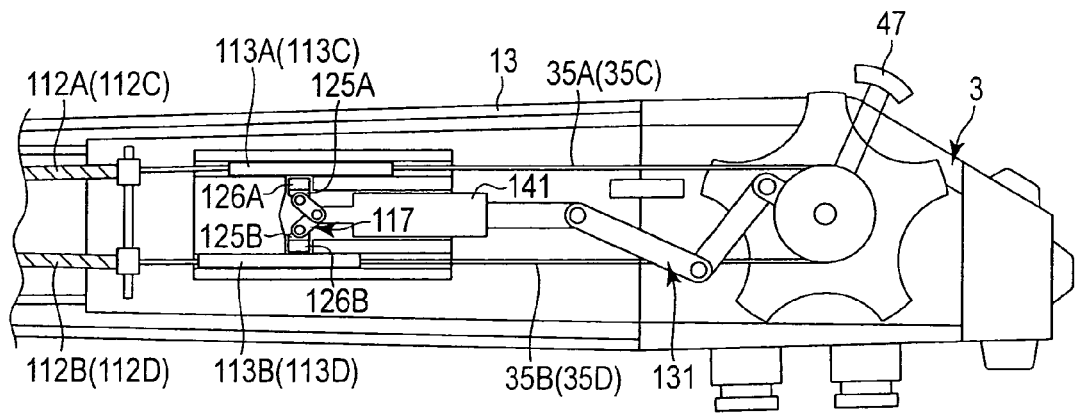
F I G. 27
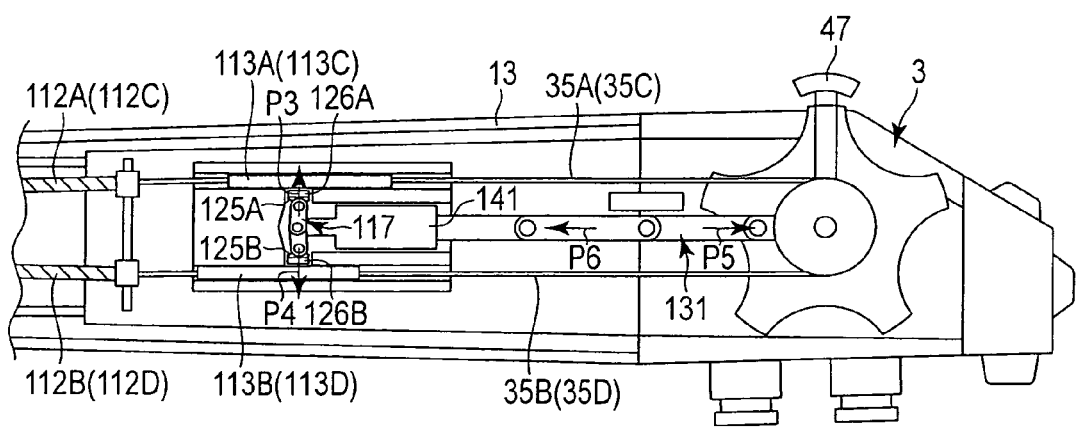
F I G. 28

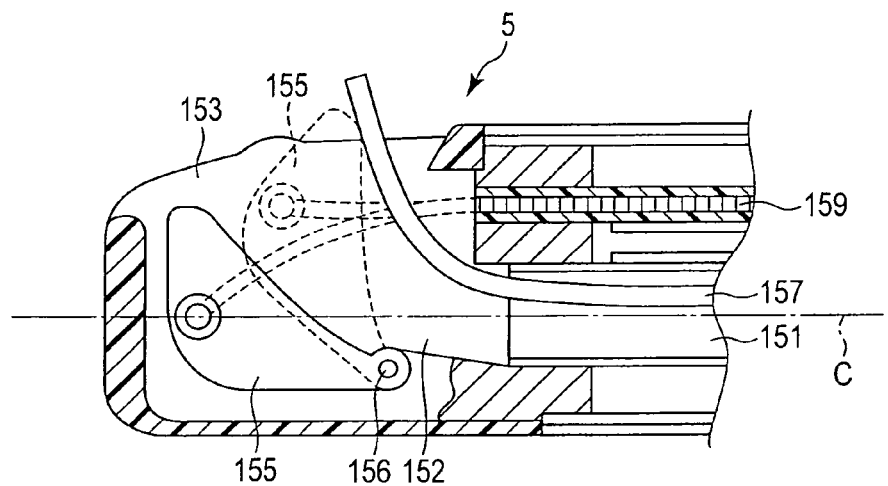
F I G. 29
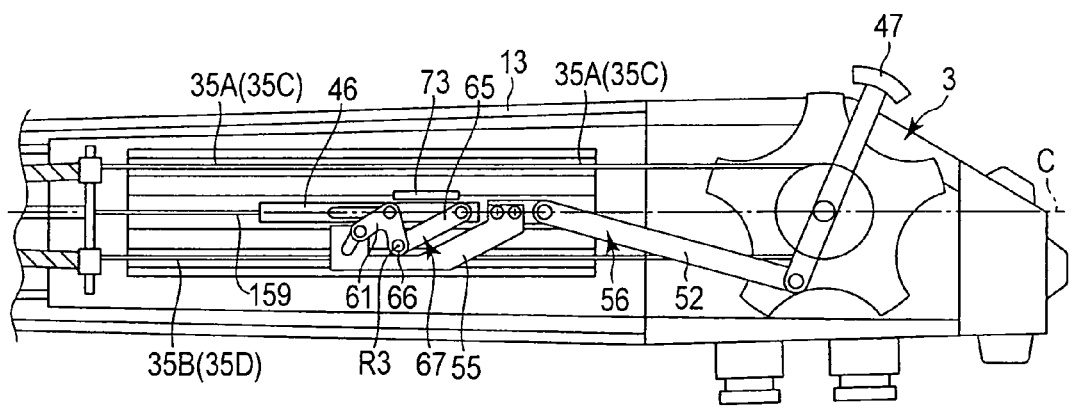
F I G. 30

INSERTION APPARATUS

CROSS-REFERENCE TO RELATED APPLICATIONS

This is a Continuation Application of PCT Application No. PCT/JP2012/064899, filed Jun. 11, 2012 and based upon and claiming the benefit of priority from prior Japanese Patent Application No. 2011-157093, filed Jul. 15, 2011, the entire contents of which are incorporated herein by reference.

BACKGROUND OF THE INVENTION

1. Field of the Invention

The present invention relates to an insertion apparatus, for example an endoscope, including an insertion section configured to be inserted into a body cavity or a pipe. More particularly, the present invention relates to an insertion apparatus including a fixing mechanism configured to prevent an intended motion state of a motion portion in an insertion section from being readily released by an external force that acts on the motion portion when maintaining the motion portion in the insertion section in the intended motion state.

2. Description of the Related Art

As an insertion apparatus including an insertion section configured to be inserted into a body cavity, a pipe, or the like, there is, e.g., an endoscope. The endoscope is used for observation and the like of a body tissue in a body cavity in the medical field, or for observation and the like of an inner wall of a pipe in the industrial field. Such an endoscope includes a holding section (a grip) provided to a proximal direction side of an insertion section. In the holding section are provided with a knob configured to perform a bending operation of a bending section, and various operation input portions such as an air supply/water supply switch of the bending section.

As such operation input portions, there are a lever configured to perform an operation of fixing and holding a bent state of the bending section at a desired position and a hardness adjustment knob configured to change a hardness of a flexible tube section provided on a part to the proximal direction side of the bending section in the insertion section as disclosed in Jpn. Pat. Appln. KOKAI Publication No. Hei 9-294710, and others. In the endoscope according to Jpn. Pat. Appln. KOKAI Publication No. Hei 9-294710, a hardness adjustment knob is provided on a holding section. Further, in the insertion section, a hardness adjustment wire is extended along a longitudinal axis. A distal end of the hardness adjustment wire is fixed between a bending section and a flexible tube section. A proximal end of the hardness adjustment wire is wound around a pulley provided in the holding section. Furthermore, the hardness adjustment wire is inserted through a coil pipe extended in the insertion section along the longitudinal axis. A distal end of the coil pipe is fixed to a distal end portion of the hardness adjustment wire. A proximal end of the coil pipe is fixed to an inner peripheral portion of the holding section.

At the time of hardening the flexible tube section, the pulley is rotated by hardness adjustment using the hardness adjustment knob. As a result, the hardness adjustment wire is pulled. When the hardness adjustment wire is pulled, the coil pipe shrinks (contracts) in directions parallel to the longitudinal axis. When the coil pipe shrinks, the flexible tube section is hardened.

BRIEF SUMMARY OF THE INVENTION

According to one aspect of invention, an insertion apparatus includes that an insertion section which includes a motion portion at a distal end portion thereof, and which is extended along a longitudinal axis; a holding section which is provided to a proximal direction side of the insertion section; a transmitting portion configured to transmit, to the motion portion, input of an operation of performing a motion in the motion portion; an interlocking movement member configured to move along the longitudinal axis with respect to the holding section in tandem with the motion of the motion portion; a switching operating section which is configured to perform a switching operation of a state of the motion portion between a state that the motion portion performs the motion in response to the input of the operation and a state that the motion of the motion portion is regulated irrespective of the input of the operation; a moving unit which is configured to move in accordance with the switching operation between a first movement position in the state that the motion portion performs the motion and a second movement position in the state that the motion of the motion portion is regulated; a link unit including: a first link; a second link which is attached to the first link at a link coupling position; and a coupling portion which couples the first link with the second link to allow their pivotal movement with respect to each other about the link coupling position in a state that the first link and the second link form a substantially V-like shape having the link coupling position as an apex when the moving unit is placed at the first movement position and in a state that the first link and the second link form a substantially linear shape that does not bend at the link coupling position when the moving unit is placed at the second movement position; and a regulating portion which configured to regulate movement of the interlocking movement member along the longitudinal axis, and configured to fix and hold the motion portion when the first link and the second link of the link unit form the substantially linear shape.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a schematic view showing an internal configuration of a holding case of a holding section in the endoscope according to a first embodiment;

FIG. 9 is a schematic view showing a mechanism configured to transmit a switching operation of a switching operation lever when the second bending section in the endoscope according to the first embodiment is the movable state;

FIG. 10 is a schematic view showing the mechanism configured to transmit the switching operation of the switching operation lever when the second bending section in the endoscope according to the first embodiment is the fixed state;

FIG. 12 is a cross-sectional view taken along a line 12-12 in FIG. 11;

FIG. 13 is a cross-sectional view taken along a line 13-13 in FIG. 11;

FIG. 21 is a cross-sectional view taken along a line 21-21 in FIG. 20;

FIG. 22 is a schematic view showing an internal configuration of a holding case when the first bending section in the endoscope according to the third embodiment is a movable state;

FIG. 23 is a schematic view showing the internal configuration of the holding case when the first bending section in the endoscope according to the third embodiment is a fixed state;

FIG. 24 is a perspective view schematically showing configurations of a slide member and a brake caliper in the endoscope according to the third embodiment;

FIG. 27 is a schematic view showing an internal configuration of a holding case when a first bending section of an endoscope according to a modification of the fourth embodiment is a movable state;

FIG. 28 is a schematic view showing the internal configuration of the holding case when the first bending section in the endoscope according to the modification of the fourth embodiment is a fixed state;

FIG. 29 is a cross-sectional view schematically showing a configuration of a distal hard section in an endoscope according to a fifth embodiment of the present invention;

FIG. 30 is a schematic view showing an internal configuration of a holding case when a treatment tool raiser in the endoscope according to the fifth embodiment is a movable state;

DETAILED DESCRIPTION OF THE INVENTION (First Embodiment)

A first embodiment according to the present invention will now be described with reference to FIG. 1 to FIG. 10.

Figure 1:
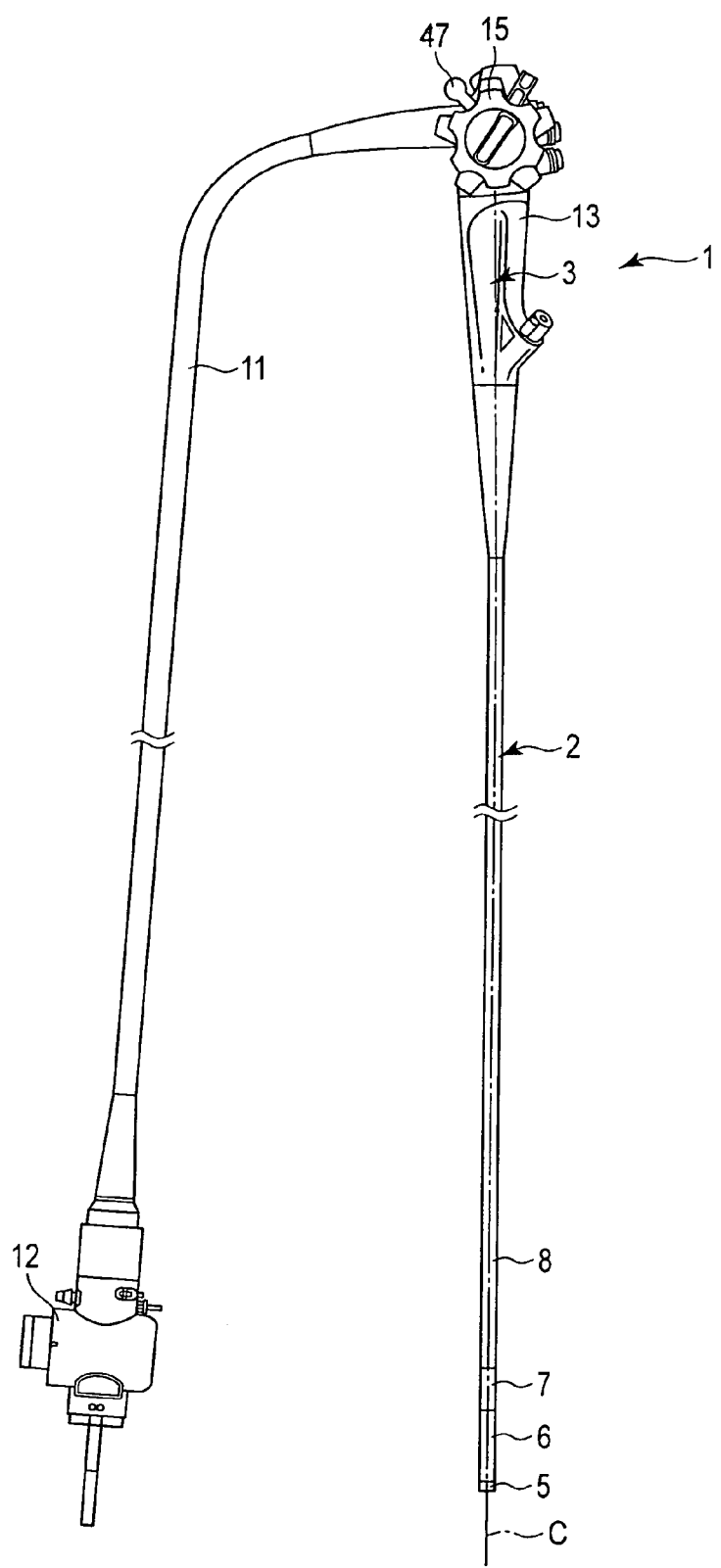
FIG. 1 is a schematic view showing an endoscope according to a first embodiment of the present invention.

FIG. 1 shows a configuration of an endoscope 1 which is an insertion apparatus. The endoscope 1 is a medical endoscope 1 used in the medical field. As shown in FIG. 1, the endoscope 1 includes an insertion section 2 extended along a longitudinal axis C, and a holding section 3 provided to a proximal direction side of the insertion section 2. The insertion section 2 includes a distal hard section 5, a first bending section 6 provided to the proximal direction side of the distal hard section 5, a second bending section 7 provided to the proximal direction side of the first bending section 6, and an elongated flexible tube section 8 provided to the proximal direction side of the second bending section 7.

One end of a universal cord 11 is connected to the holding section 3. A scope connector 12 is provided at the other end of the universal cord 11. The universal cord 11 is connected to peripheral units (not shown) such as an image processing unit or a light source unit via the scope connector 12. The holding section 3 includes a holding case 13 which is a cladding (sheath). A bending operation knob 15, which is a bending operating section, is provided to the holding case 13. When an operation is input using the bending operation knob 15, the first bending section 6 performs a bending motion.

Figure 2:
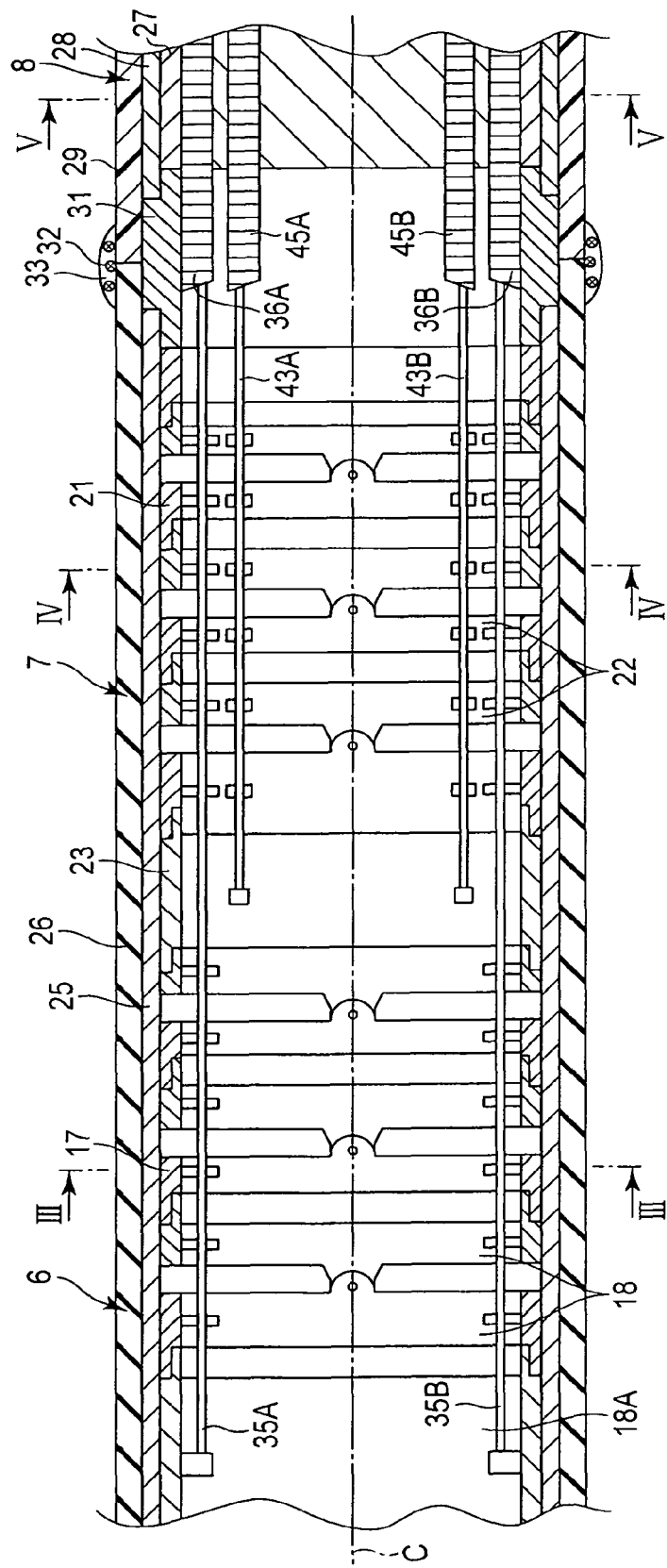
FIG. 2 is a cross-sectional view schematically showing a first bending section, a second bending section, and a flexible tube section of the endoscope according to the first embodiment.
Figure 3:
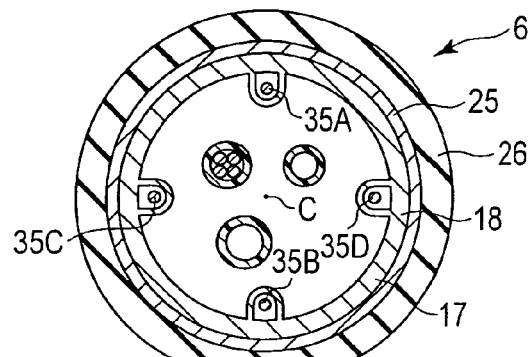
FIG. 3 is a cross-sectional view taken along a line in FIG. 2.
Figure 4:
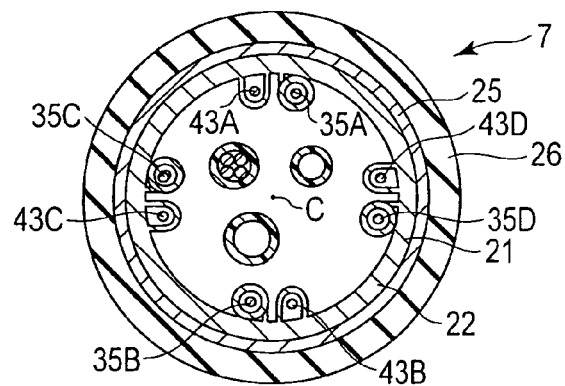
FIG. 4 is a cross-sectional view taken along a line IV-IV in FIG. 2.
Figure 5:
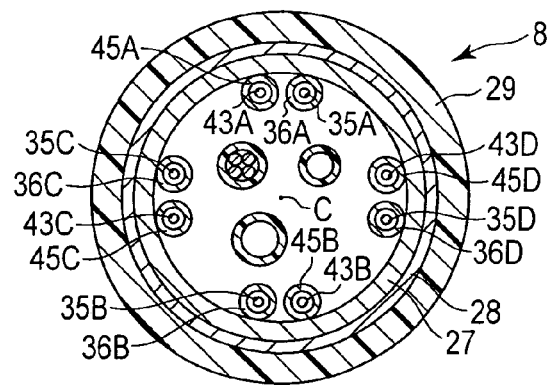
FIG. 5 is a cross-sectional view taken along a line V-V in FIG. 2.

FIG. 2 is a view showing configurations of the first bending section 6, the second bending section 7 and the flexible tube section 8. FIG. 3 is a cross-sectional view taken along a line in FIG. 2, and FIG. 4 is a cross-sectional view taken along a line IV-IV in FIG. 2. Furthermore, FIG. 5 is a cross-sectional view taken along a line V-V in FIG. 2. As shown in FIG. 2, the first bending section 6 includes a first bending tube 17. The first bending tube 17 includes first bending pieces 18 aligned along the longitudinal axis C. Each first bending piece 18 is coupled with a first bending piece 18 adjacent thereto so that these pieces can pivotally move with respect to each other. The second bending section 7 includes a second bending tube 21. The second bending tube 21 includes second bending pieces 22 aligned along the longitudinal axis C. Each second bending piece 22 is coupled with a second bending piece 22 adjacent thereto so that these pieces can pivotally move with respect to each other. The first bending tube 17 is coupled with the second bending tube 21 via a connection mouth ring 23. A first reticular tube (a first blade) 25 made of a metal is provided to an outer peripheral direction side of the first bending tube 17 and the second bending tube 21. A part to the outer peripheral direction side of the first reticular tube 25 is covered with a first envelope 26 made of rubber.

The flexible tube section 8 includes a helical tube (a flex) 27 made of a metal. A second reticular tube (a second blade) 28 made of a metal is provided to the outer peripheral direction side of the helical tube 27. A part to the outer peripheral direction side of the second reticular tube 27 is covered with a second envelope 29 made of a resin. The second bending tube 21 and the first reticular tube 25 are coupled with the helical tube 27 and the second reticular tube 28 via a connection mouth ring 31. A string 32 is wound around an outer peripheral portion of the first envelope 26 and an outer peripheral portion of the second envelope 29, and these outer peripheral portions are covered with an adhesive 33 between the first envelope 26 and the second envelope 29.

As shown in FIG. 2, distal ends of four bending operation wires 35A to 35D as linear members are fixed to a first bending piece 18A that is provided on the most distal direction side in the first bending pieces 18. The respective bending operation wires 35A to 35D are extended in the insertion section 2 along the longitudinal axis C. As shown in FIG. 3, each of the bending operation wires 35A to 35D is arranged approximately 90° away from the neighboring bending operation wires 36A to 36D around the longitudinal axis C.

As shown in FIG. 2, in the insertion section 2, four first coil pipes 36A to 36D are extended along the longitudinal axis C. Distal ends of the respective first coil pipes 36A to 36D are fixed to the connection mouth ring 31. As shown in FIG. 4, each of the first coil pipes 36A to 36D is arranged substantially 90° away from the neighboring first coil pipes 36A to 36D around the longitudinal axis C. Each of the bending operation wires 35A to 35D is inserted through the corresponding first coil pipe 36A to 36D.

FIG. 6 is a view showing an internal configuration of the holding section 3. As shown in FIG. 6, a substrate 37 is fixed to an inner peripheral portion of the holding case 13. A plate-shaped member 39 is fixed to the substrate 37. Proximal ends of the respective first coil pipes 36A to 36D are fixed to the plate-shaped member 39. The respective bending operation wires 35A and 35D are extended to the proximal direction side of the plate-shaped member 39. Moreover, pulleys 41A and 41B are provided in the holding case 13. The proximal ends of the bending operation wires 35A and 35B are fixed to the pulley 41A. The proximal ends of the bending operation wires 35C and 35D are fixed to the pulley 41B. When an operation is input using the bending operation knob 15, the pulleys 41A and 41B are rotated. When the pulley 41A is rotated, the bending operation wire 35A or the bending operation wire 35B is pulled. As a result, the first bending section 6 performs a bending motion in, e.g., up-and-down directions. Additionally, when the pulley 41B is rotated, the bending operation wire 35C or the bending operation wire 35D is pulled. As a result, the first bending section 6 carries out a bending morion in, e.g., left-and-right directions.

Further, as described above, in the second bending section 7, the second bending tube 21, the first reticular tube 25, and the first envelope 26 are sequentially arranged from the inner peripheral direction side. Therefore, the second bending section 7 has flexibility. Therefore, when an external force functions owing to bending of the first bending section 6, the second bending section 7 is bent. That is, to follow the bending motion of the first bending section 6, the second bending section 7 caries out the bending motion. As described above, the second bending section 7 is a motion portion configured to perform a bending motion when an operation is input through the bending operation knob 15. Furthermore, the bending operation wires 35A to 35D are transmitting portions configured to transmit the operation input to the second bending section 7.

As shown in FIG. 2, in the inserting section 2, four bending fixing wires 43A to 43D are extended along the longitudinal axis C. Distal ends of the respective bending fixing wires 43A to 43D are fixed to the connection mouth ring 23. As shown in FIG. 4, each of the bending fixing wires 43A to 43D is arranged substantially 90° away from the neighboring bending fixing wires 43A to 43D around the longitudinal axis C.

As shown in FIG. 2, in the inserting section 2, four second coil pipes 45A to 45D are extended along the longitudinal axis C. Distal ends of the respective coil pipes 45A to 45D are fixed to the connection mouth ring 31. As shown in FIG. 5, each of the second coil pipes 45A to 45D is arranged approximately 90° apart from their neighboring second coil pipes 45A to 45D around the longitudinal axis C. Each of the bending fixing wires 43A to 43D are inserted through the corresponding second coil pipe 45A to 45D.

As shown in FIG. 6, proximal ends of the respective second coil pipes 45A to 45D are fixed to the plate-shaped member 39. The respective bending fixing wire 43A to 43D are extended to the proximal direction side of the plate-shaped member 39. Furthermore, in the holding case 13, a bar-shaped member 46 is provided. Proximal ends of the bending fixing wires 43A to 43D are fixed to the bar-shaped member 46. The respective bending fixing wires 43A to 43D move along the longitudinal axis C with respect to the holding case 13 in accordance with the bending motion of the second bending section 7. That is, the respective bending fixing wires 43A to 43D are interlocking movement members configured to move along the longitudinal axis C with respect to the holding case 13 in tandem with the bending motion of the second bending section 7 which is a motion portion.

As shown in FIG. 1 and FIG. 6, a switching operation lever 47 which is a switching operating section is provided to the holding case 13. The switching operation lever 47 is configured to switch a state of the second bending section 7, which is the motion portion, between a movable state and a fixed state. When the second bending section 7 is in the movable state, applying acting force F1 to the switching operation lever 47 allows the switching operation to the fixed state to be performed. Moreover, when the second bending section 7 is in the fixed state, applying acting force F'1, whose direction is opposite to that of the acting force F1, to the switching operation lever 47 allows the switching operation to the movable state to be performed.

Figure 7:
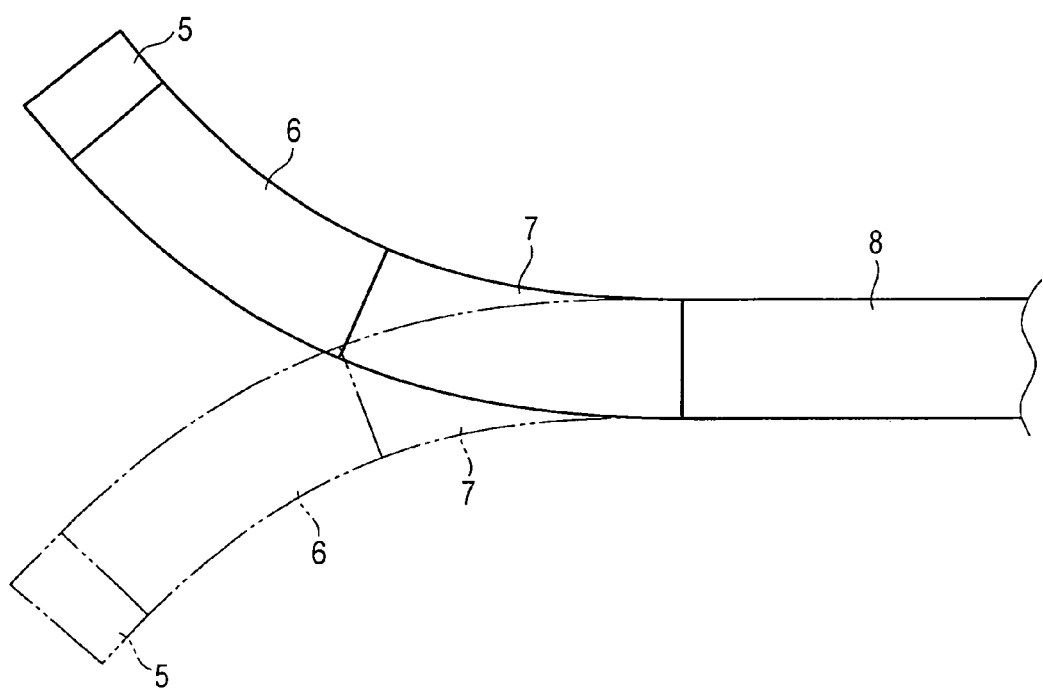
FIG. 7 is a schematic view showing motion states of the first bending section and the second bending section when the second bending section of the endoscope according to the first embodiment is a movable state.
Figure 8:
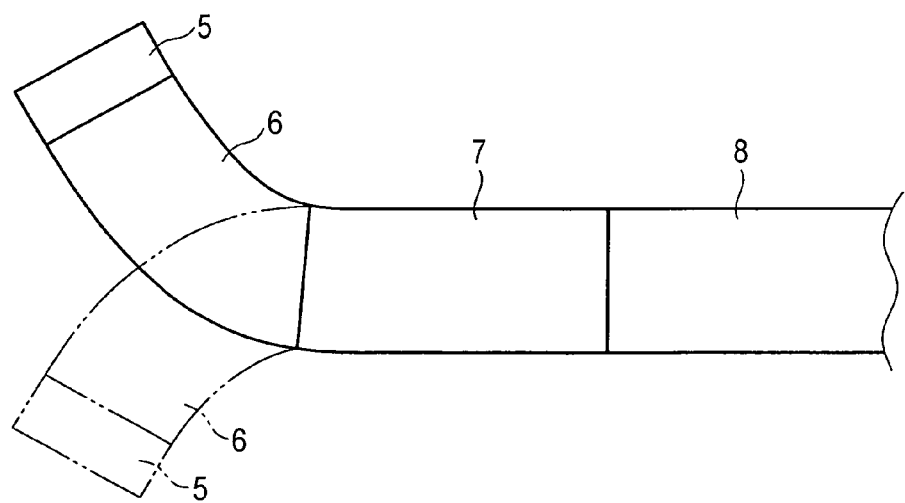
FIG. 8 is a schematic view showing motion states of the first bending section and the second bending section when the second bending portion of the endoscope according to the first embodiment is a fixed state.

FIG. 7 is a view showing motion states of the first bending section 6 and the second bending section 7 when the second bending section 7 is the movable state, and FIG. 8 is a view showing motion states of the first bending section 6 and the second bending section 7 when the second bending section 7 is the fixed state. As shown in FIG. 7, when the second bending section 7 is the movable state, input of an operation through the bending operation knob 15 allows the first bending section 6 to bend. Further, the second bending section 7 performs the bending motion to follow the bending motion of the first bending section 6. Moreover, as shown in FIG. 8, when the second bending section 7 is the fixed state, the second bending section 7 is fixed and held irrespective of input of an operation through the bending operation knob 15, and it does not perform the bending motion. That is, the second bending section 7 is fixed and held in a straight state without bending. Therefore, in response to input of an operation through the bending operation knob 15, the first bending portion 6 alone performs the bending motion.

FIG. 9 and FIG. 10 are views showing a mechanism configured to transmit a switching operation using the switching operation lever 47. The second bending section 7 is the movable state in a state shown in FIG. 9, and the second bending section 7 is the fixed state in a state shown in FIG. 10. As shown in FIG. 6, FIG. 9, and FIG. 10, the switching operation lever 47 includes a first lever end 49A and a second lever end 49B provided on the opposite side of the first lever end 49A. The acting force (first acting force) F1 or the acting force (the first acting force) F'1 is applied to the first lever end 49A of the switching operation lever 47 from an operator by a switching operation. Further, the switching operation lever 47 is attached to a shaft member 51 between the first lever end 49A and the second lever end 49B. The switching operation lever 47 pivots (revolves) about a pivoting axis R1 of the shaft member 51 by the switching operation. A slide member 52 is attached to the second lever end 49B of the switching operation lever 47. When the acting force F1 acts on the first lever end 49A of the switching operation lever 47, acting force (second acting force) F2 acts on the slide member 52 from the second lever end 49. When the acting force F'1 acts on the first lever end 49A of the switching operation lever 47, acting force (the second acting force) F'2, whose direction is opposite to that of the acting force F2, acts on the slide member 52 from the second lever end 49B.

Here, a dimension A1 between the pivoting axis R1 and the first lever end 49A is larger than a dimension A2 between the pivoting axis R1 and the second lever end 49B. Therefore, when the switching operation is performed, the acting force F2 is larger than the acting force F1. That is, the acting force (the second acting force) F2 acting on the slide member (a second member) 52 from the switching operation lever (the first member) 47 is larger than the acting force (the first acting force) F1 acting on the switching operation lever (a first member) 47. As described above, the switching operation lever 47 and the slide member 52 serve as a force amplifying unit 53 configured to amplify the acting force (the second acting force) F2 to be higher than the acting force (the first acting force) F1. Likewise, the switching operation lever 47 and the slide member 52 amplify (increase) the acting force (the second acting force) F'2 to be higher than the acting force (the first acting force) F'1.

As shown in FIG. 6, FIG. 9, and FIG. 10, a plate-shaped member 55 is attached to the slide member 52. The slide member 52 and the plate-shaped member 55 integrally move when the acting force (the second acting force) F2 or the acting force (the second acting force) F'2 act from the switching operation lever 47. That is, the slide member 52 and the plate-shaped member 55 form a moving unit 56 configured to move in accordance with a switching operation of the switching operation lever 47. As shown in FIG. 9, when the second bending section 7 which is the motion portion is the movable state, the moving unit 56 is placed at the first movement position. Further, as shown in FIG. 10, when the second bending section 7 is the fixed state, the moving unit 56 is placed at a second movement position. That is, the moving unit 56 moves between the first movement position and the second movement position in accordance with the switching operation of the switching operation lever 47.

An elliptic cam groove 57 is formed in the plate-shaped member 55. Furthermore, a first link 61 is attached to the plate-shaped member 55 in the cam groove 57. The first link 61 is formed into a substantially L-like shape, and includes a first link end 62A attached to the plate-shaped member 55, and a second link end 62B provided on the opposite side of the first link end 62A. A shaft member 63 is attached to a top position of the L-like shape of the first link 61. The shaft member 63 is attached to the substrate 37. When the moving unit 56 moves, acting force (the first acting force) F3 or acting force (the first acting force) F'3, whose direction is opposite to that of the acting force F3, acts on the first link end 62A of the first link 61 from the plate-shaped member 55. When the acting force F3 or the acting force F'3 acts on the first link end 62A, the first link 61 pivotally moves about a pivoting axis R2. As this time, the first link end 62A moves in the cam groove 57.

Moreover, a second link 65 is attached to the second link end 62B of the first link 61. The first link 61 is coupled with the second link 65 through a coupling portion 66. The coupling portion 66 forms a link coupling position R3 between the first link 61 and the second link 65. The first link 61 and the second link 65 pivotably move with respect to each other about the link coupling position R3. When the acting force F3 acts on the first link end 62A of the first link 61, acting force (the second acting force) F4 acts on the coupling portion 66 from the second link end 62B of the first link 61. Additionally, when the acting force F'3 acts on the first link end 62A of the first link 61, acting force (the second acting force) F'4, whose direction is opposite to that of the acting force F4, acts on the coupling portion 66 from the second link end 62B of the first link 61. As described above, the first link 61, the second link 65, and the coupling portion 66 form a link unit 67.

When the acting force (the first acting force) F3 or the acting force (the first acting force) F'3 acts on the first link 61, the first link 61 pivotally moves about the pivoting axis R2 of the shaft member 63. At this time, the pivoting axis R2 placed at a top position of the L-like shape of the first link 61 functions as a supporting point. Further, the first link end 62A functions as a power point where the acting force (the first acting force) F3 or the acting force (the first acting force) F'3 acts from the plate-shaped member 55. Furthermore, the second link end 62B serves as a working point where the acting force (the second acting force) F4 or the acting force (the second acting force) F'4 is allowed to act on the coupling portion 66. That is, the first link 61 is an L-shaped crank member having the supporting point as its apex (top).

Here, the first link end (the power point) 62A is placed away from the pivoting axis (the supporting point) R2 of the shaft member 63 by a first distance B1. Furthermore, the second link end (the working point) 62B is placed away from the pivoting axis (the supporting point) R2 of the shaft member 63 by a second distance B2. The first distance B1 is longer than the second distance B2. Therefore, when the first link 61 pivotally moves, the acting force F4 is higher than the acting force F3. That is, the acting force (the second acting force) F4 that acts on the coupling portion (the second member) 66 from the first link (the first member) 61 is higher than the acting force (the first acting force) F3 that acts on the first link (the first member) 61. As described above, the first link 61 and the coupling portion 66 form a force amplifying unit 68 configured to amplify the acting force (the second acting force) F4 to be higher than the acting force (the first acting force) F3. Likewise, the first link 61 and the coupling portion 66 amplify the acting force (the second acting force) F'4 to be higher than the acting force (the first acting force) F'3.

As shown in FIG. 9, when the moving unit 56 is placed at the first movement position, the first link 61 and the second link 65 form a substantially V-like shape having a link coupling position R3 as its apex (top). Here, at the link coupling position R3, the first link 61 and the second link 65 form a first angle α1 and a second angle α2. In a state that the first link 61 and the second link 65 form the substantially V-like shape, the first angle α1 is smaller than 180° and the second angle α2 is larger than 180°.

When the acting force F3 acts on the first link 61 from this state, the first link 61 pivotally moves about the pivoting axis R2 of the shaft member 63. Further, the acting force F4 acts on the coupling portion 66 of the link unit 67 from the first link 61. When the acting force F4 acts on the coupling portion 66, the first link 61 and the second link 65 pivotally move about the link coupling position R3 with respect to each other. As a result, at the link coupling position R3, the first angle α1 increases and approximates 180°. Furthermore, the second angle α2 decreases and approximates 180°.

Moreover, as shown in FIG. 10, when the moving unit 56 has moved to the second movement position, the first link 61 and the second link 65 form a substantially linear shape that does not bend at the link coupling position R3. In a state that the first link 61 and the second link 65 form the substantially linear shape, acting force P1 acts on the first link 61 in a direction away from the link coupling position R3. Additionally, acting force P2 acts on the second link 65 in a direction away from the link coupling position R3. The acting force P1 has the same magnitude as the acting force P2. Further, the magnitude of the acting force P1 and the acting force P2 is proportionate to tan(α1/2). In a state that the substantially linear shape is formed, since α1 is substantially 180°, α1/2 is substantially 90°. Therefore, the acting force P1 and the acting force P2 infinitely increase. As described above, the link unit 67 includes a toggle section 69 configured to make the acting force P1 to act on the first link 61 and also make the acting force P1 to act on the second link 65 in a direction away from the link coupling position R3 when the substantially linear shape is formed.

The bar-shaped member 46 is attached to the second link 65. A substantially elliptic slide hole 71 is formed in the bar-shaped member 46. The shaft member 63 is inserted through the slide hole 71. In a state that the first link 61 and the second link 65 form the substantially linear shape, the acting force P2 that acts on the second link 65 also acts on the bar-shaped member 46. At this time, a direction of the acting force P2 is substantially equal to the proximal direction, and the acting force P2 infinitely increases as described above. Therefore, the acting force P2 moves the bar-shaped member 46 toward the proximal direction. At this time, the slide hole 71 moves in the proximal direction with respect to the shaft member 63. It is to be noted that the acting force P2 infinitely increases, and hence the bar-shaped member 46 moves toward the proximal direction. Therefore, for example, in the state that the first link 61 and the second link 65 form the substantially V-like shape, when the acting force that acts on the bar-shaped member 46 is zero or small (it does not infinitely increase), the bar-shaped member 46 does not move.

When the bar-shaped member 46 moves in the proximal direction, a pulling force, which is regulating force, acts on the bending fixing wires 43A to 43D. As a result, the bending fixing wires 43A to 43D are pulled in the proximal direction. When the bending fixing wires 43A to 43D are pulled, the bending fixing wires 43A to 43D are held in the tensed state, and the movement of the bending fixing wires 43A to 43D along the longitudinal axis C is regulated. That is, the bar-shaped member 46 serves as a regulating portion configured to regulate the movement of the bending fixing wires 43A to 43D along the longitudinal axis C. Further, when the respective bending fixing wires 43A to 43D are pulled, the second bending section 7 is fixed and held in the straight state without bending.

Furthermore, when the first link 61 and the second link 65 form the substantially linear shape, the acting force P1 and the acting force P2 infinitely increase. Therefore, the acting force P1 that infinitely increases acts on the first link 61 in the direction away from the link coupling position R3, and the acting force P2 that infinitely increase acts on the second link 65 in the direction away from the link coupling position R3. Therefore, the acting force P1 and the acting force P2 generated by the toggle section 69 hold the substantially linear shape at the link coupling position R3.

Moreover, in a state that the second bending section 7, which is the motion portion, is fixed and held, a reaction force of the force of fixing and holding the second bending section 7 functions. Therefore, a reaction force of the pulling force (the regulating force) functions on the bar-shaped member 46 from the bending fixing wires 43A to 43D which are the interlocking movement members. Here, when the acting force P2 acts on the bar-shaped member 46, the bar-shaped member 46 moves in the proximal direction, and the pulling force, which is the regulating force, acts on the bending fixing wires 43A to 43D from the bar-shaped member 46. Further, the movement of the bending fixing wires 43A to 43D along the longitudinal axis C is restricted. Since the acting force P2 infinitely increase, the pulling force of the bending fixing wires 43A to 43 increases. When the pulling force which is the regulating force increases, the movement of the bending fixing wires 43A to 43D along the longitudinal axis C is assuredly regulated, and the second bending section 7 is assuredly fixed and held.

Furthermore, since the acting force P2 infinitely increases, the reaction force of the pulling force (regulating force) from the bending fixing wires 43A to 43D is absorbed. Moreover, as described above, the acting force P1 and the acting force P2 hold the substantially linear shape at the link coupling position R3. Therefore, when the substantially linear shape is formed at the link coupling position R3, an operator does not have to constantly apply the acting force F1 to the switching operation lever 47 in order to avoid a change of the second bending section 7 to the movable state due to the reaction force of the pulling force. That is, even when the operator does not apply the acting force F1 to the switching operation lever 47, the state that the substantially linear shape is formed at the link coupling position R3 is held. Therefore, when the second bending section 7 is fixed, operability of, e.g., input of an operation of bending the first bending section 6 is improved. That is, when the second bending section 7 is the fixed state, the operability of operations other than fixing and holding the second bending section 7 is improved.

Moreover, the force amplifying unit 53 (the switching operation lever 47, the slide member 52) amplifies the acting force (the second acting force) F2 acting on the slide member 52 from the switching operation lever 47 to be higher than the acting force (the first acting force) F1 applied to the switching operation lever 47 by the operator. When the acting force F2 is higher than the acting force F1, the pulling force of the bending fixing wires 43A to 43D which is the regulating force is amplified. Additionally, the force amplifying unit 68 (the first link 61, the coupling portion 66) amplifies the acting force (the second acting force) F4 acting on the coupling portion 66 from the first link 61 to be higher than the acting force (the first acting force) F3 acting on the first link 61 from the plate-shaped member 55. When the acting force F4 is higher than the acting force F3, the pulling force of the bending fixing wires 43A to 43D which is the regulating force is amplified.

As shown in FIG. 6, a stopper member 73 is provided in the holding case 13. The stopper member 73 is fixed to the substrate 37. When the link unit 67 has changed from the state that the substantially V-like shape with the first angle α1 smaller than 180° and the second angle α2 larger than 180° is formed at the link coupling position R3 to the state that the substantially linear shape is formed at the link coupling position R3, the link unit 37 comes into contact with the stopper member 73 at the link coupling position R3. When the link unit 67 comes into contact with the stopper member 73 at the link coupling position R3, the change of the link unit 67 to a state that an inverted V-like shape with the first angle α1 larger than 180° and the second angle α2 smaller than 180° is formed at the link coupling position R3 can be avoided. As a result, the link unit 67 is further assuredly held in the state that the substantially linear shape is formed at the link coupling position R3. When the substantially linear state is held, the acting force P1 that infinitely increases acts on the first link 61, and the acting force P2 that infinitely increases acts on the second link 65. As a result, the bending fixing wires 43A to 43D are pulled with a sufficiently larger pulling force.

Furthermore, in the link unit 67 in the state that the substantially linear shape is formed, the first angle α1 is larger than 180° and smaller than 185°, and the second angle α2 is larger than 175° and smaller than 180°. That is, the first angle α1 is slightly larger than 180°, and the second angle α2 is slightly smaller than 180°. As a result, the link unit 67 hardly changes to a state that the first link 61 and the second link 65 form the substantially V-like shape that the first angle α1 is smaller than 180° and the second angle α2 is larger than 180°. Therefore, the link unit 67 is further assuredly held in the state that the substantially linear shape is formed at the link coupling position R3.

Moreover, when the second bending section 7 has been switched from the fixed state to the movable state by the switching operation using the switching operation lever 47, the moving unit 56 (the slide member 52, the plate-like member 55) moves from the second movement position to the first movement position. As a result, the acting force F'3 acts on the first link 61, and the first link 61 pivotally moves about the pivoting axis R2 of the shaft member 63. Additionally, the acting force F'4 acts on the coupling portion 66 of the link unit 67 from the first link 61. When the acting force F'4 acts on the coupling portion 66, the first link 61 and the second link 65 bend with respect to each other at the link coupling position R3. At this time, the first angle α1 is smaller than 180°, and the second angle α2 is larger than 180°. Since a direction of the acting force F'4 is different from a direction of the acting force P1 and a direction of the acting force P2, even if the acting fore F'4 is small, the first link 61 and the second link 65 can easily bend with respect to each other at the link coupling position R3. That is, even if the acting force F'1 applied by an operator using the switching operation lever 47 is small, the first link 61 and the second link 65 can easily bend with respect to each other at the link coupling position R3.

Further, when the first link 61 and the second link 65 bend with respect to each other at the link coupling position R3, the substantially linear shape is not formed at the link coupling position R3. Therefore, the acting force P2 that infinitely increases does not act on the link unit 67, and a reaction force of the pulling force (the regulating force) from the bending fixing wires 43A to 43D is not absorbed. Therefore, the reaction force of the pulling force changes the state of the link unit 67 to the state that the first link 61 and the second link 65 form the substantially V-like shape at the link coupling position R3. As described above, even if the acting force F'1 applied by the operator using the switching operation lever 47 is small, the second bending section 7 is easily switched to the movable state.

Therefore, the endoscope 1 which is the insertion apparatus having the above-described configuration exercises the following effect. That is, in the endoscope 1, when the first link 61 and the second link 65 form the substantially linear shape, the acting force P1 and the acting force P2 infinitely increase. Therefore, the acting force P1 that infinitely increases acts on the first link 61 in the direction away from the link coupling position R3, and the acting force P2 that infinitely increases acts on the second link 65 in the direction away from the link coupling position R3. Thus, the acting force P1 and the acting force P2 generated by the toggle section 69 can hold the substantially linear shape at the link coupling position R3.

Further, in the state that the second bending section 7 that is the motion portion is fixed and held, a reaction force of the force of fixing and holding the second bending section 7 acts. Therefore, a reaction force of the pulling force (the regulating force) acts on the bar-shaped member 46 from the bending fixing wires 43A to 43D which are the interlocking movement members. Here, when the acting force P2 acts on the bar-shaped member 46, the bar-shaped member 46 moves in the proximal direction, and the pulling force which is the regulating force acts on the bending fixing wires 43A to 43D from the bar-shaped member 46. Furthermore, the movement of the bending fixing wires 43A to 43D along the longitudinal axis C is restricted. Since the acting force P2 infinitely increases, the pulling force of the bending fixing wires 43A to 43D increases. When the pulling force which is the regulating force increases, the movement of the bending fixing wires 43A to 43D along the longitudinal axis C is assuredly regulated, and the second bending section 7 can be assuredly fixed and held in a desired motion state.

Moreover, since the acting force P2 infinitely increases, the reaction force of the pulling force (the regulating force) from the bending fixing wires 43A to 43D is absorbed. Additionally, as described above, the acting force P1 and the acting force P2 can hold the substantially linear shape at the link coupling position R3. Thus, when the substantially linear shape is formed at the link coupling position R3, to avoid the change of the second bending section 7 to the movable state due to the reaction force of the pulling force, an operator does not have to constantly apply the acting force F1 to the switching operation lever 47. That is, even if the operator does not apply the acting force F1 to the switching operation lever 47, the state that the substantially linear shape is formed at the link coupling position R3 can be maintained. Accordingly, when the second bending section 7 is the fixed state, for example, an operation of bending the first bending section 6 can be efficiently input. That is, when the second bending section 7 is the fixed state, operations other than fixing and holding the second bending section 7 can be efficiently carried out.

Additionally, the force amplifying unit 53 (the switching operation lever 47, the slide member 52) increases the acting force (the second acting force) F2 that acts on the slide member 52 from the switching operation lever 47 to be higher than the acting force (the first acting force) F1 that is applied to the switching operation lever 47 by an operator. When the acting force F2 is higher than the acting force F1, the pulling force of the bending fixing wires 43A to 43D which is the regulating force is amplified. Further, the force amplifying unit 68 (the first link 61, the coupling portion 66) increases the acting force (the second acting force) F4 that acts on the coupling portion 66 from the first link 61 to be higher than the acting force (the first acting force) F3 that acts on the first link 61 from the plate-shaped member 55. When the acting force F4 is higher than the acting force F3, the pulling force of the bending fixing wires 43A to 43D which is the regulating force is amplified. As described above, the force amplifying unit 53 and the force amplifying unit 68 can further assuredly regulate the movement of the bending fixing wires 43A to 43D along the longitudinal axis C.

Furthermore, when the link unit 67 has changed from the state that the substantially V-like shape having the first angle α1 smaller than 180° and the second angle α2 larger than 180° is formed at the link coupling position R3 to the state that the substantially linear shape is formed at the link coupling position R3, the link unit 67 comes into contact with the stopper member 73 at the link coupling position R3. When the link unit 67 comes into contact with the stopper member 73 at the link coupling position R3, it is possible to avoid the change of the link unit 67 to the state that the inverted V-like shape having the first angle α1 larger than 180° and the second angle smaller than 180° is formed at the link coupling position R3. As a result, the link unit 67 is further assuredly held in the state that the substantially linear shape is formed at the link coupling position R3. When the substantially linear shape is held, the acting force P1 that infinitely increases acts on the first link 61, and the acting force P2 that infinitely increases acts on the second link 65. As a result, the bending fixing wires 43A to 43D can be pulled with the sufficiently large pulling force.

Moreover, in the link unit 67 that is in the state that the substantially linear shape is formed, the first angle α1 is slightly larger than 180°, and the second angle α2 is slightly smaller than 180°. As a result, the link unit 67 hardly changes to the state that the first link 61 and the second link 65 form the substantially V-like shape with the first angle α1 smaller than 180° and the second angle α2 larger than 180°. Therefore, the link unit 67 can be further assuredly held in the state that the substantially linear shape is formed at the link coupling position R3.

(Second Embodiment)

A second embodiment will now be described with reference to FIG. 11 to FIG. 18. It is to be noted that like reference numerals denote the same parts or parts having the same functions as those in the first embodiment, and a description thereof will be omitted.

Figure 11:
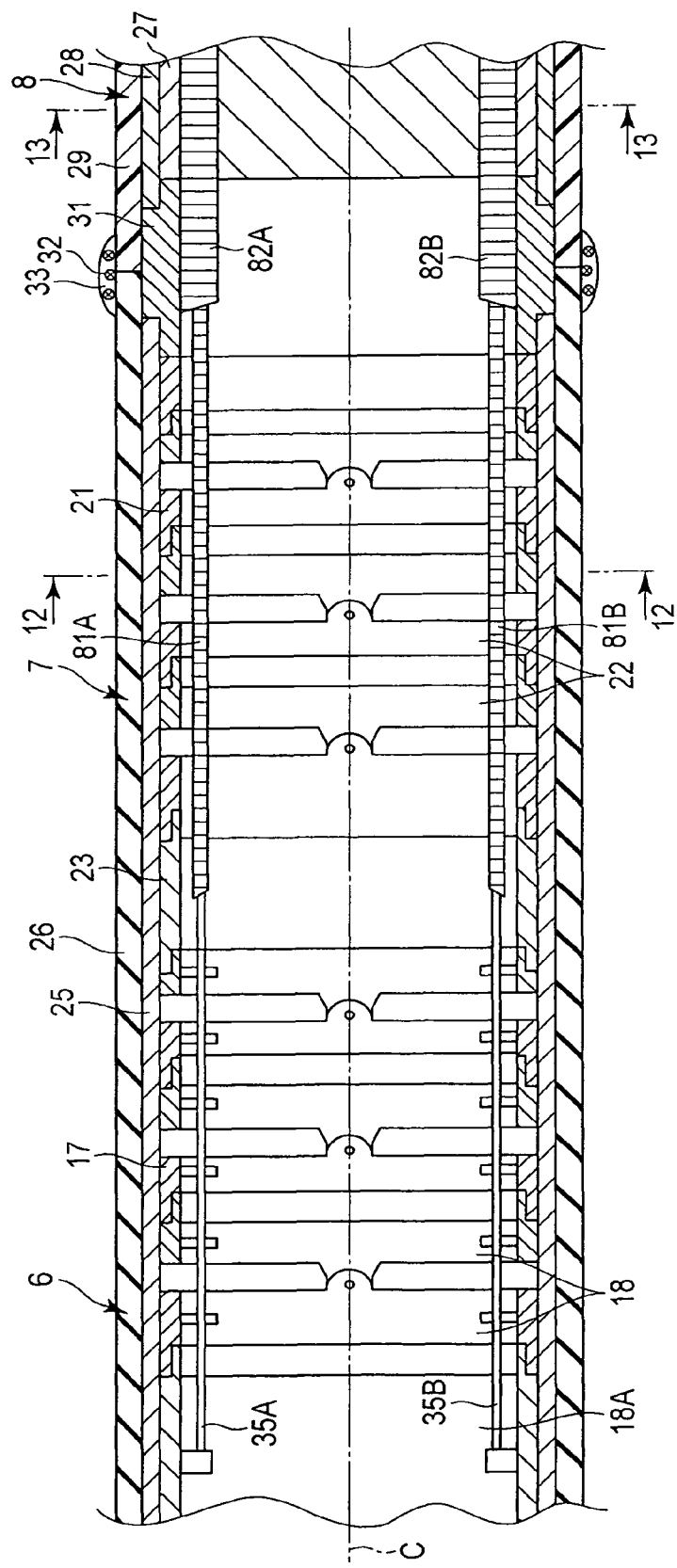
FIG. 11 is a cross-sectional view schematically showing a first bending section, a second bending section, and a flexible tube section according to a second embodiment of the present invention.

FIG. 11 is a view showing configurations of a first bending section 6, a second bending section 7, and a flexible tube section 8. FIG. 12 is a cross-sectional view taken along a line 12-12 in FIG. 11, and FIG. 13 is a cross-sectional view taken along a line 13-13 in FIG. 11. As shown in FIG. 11, an insertion section 2 of an endoscope 1 that is an insertion apparatus according to this embodiment includes a first bending section 6, a second bending section 7, and a flexible tube section 8 like the first embodiment. In the first bending section 6, distal ends of four bending operation wires 35A to 35D are fixed to a first bending piece 18A placed on the most distal direction side in first bending pieces 18. Further, four first coil pipes 81A to 81D are extended along a longitudinal axis C in the insertion section 2. Distal ends of the respective first coil pipes 81A to 81D are fixed to a connection mouth ring 23 between the first bending section 6 and the second bending section 7. As shown in FIG. 12, each of the first coil pies 81A to 81D is arranged substantially 90° away from the neighboring first coil pipes 81A to 81D around the longitudinal axis C. Each of the bending operation wires 35A to 35D is inserted through the corresponding first coil pipe 81A to 81D.

Moreover, in the insertion section 2, four second coil pipes 82A to 82D are extended along the longitudinal axis C. Distal ends of the respective second coil pipes 82A to 82D are fixed to a connection mouth ring 31 between the second bending section 7 and the flexible tube section 8. As shown in FIG. 13, each of the second coil pipes 82A to 82D is arranged substantially 90° away from the neighboring coil pipes 82A to 82D around the longitudinal axis C. Each of the coil pipes 81A to 81D is inserted through the corresponding second coil pipe 82A to 82D.

Figure 14:
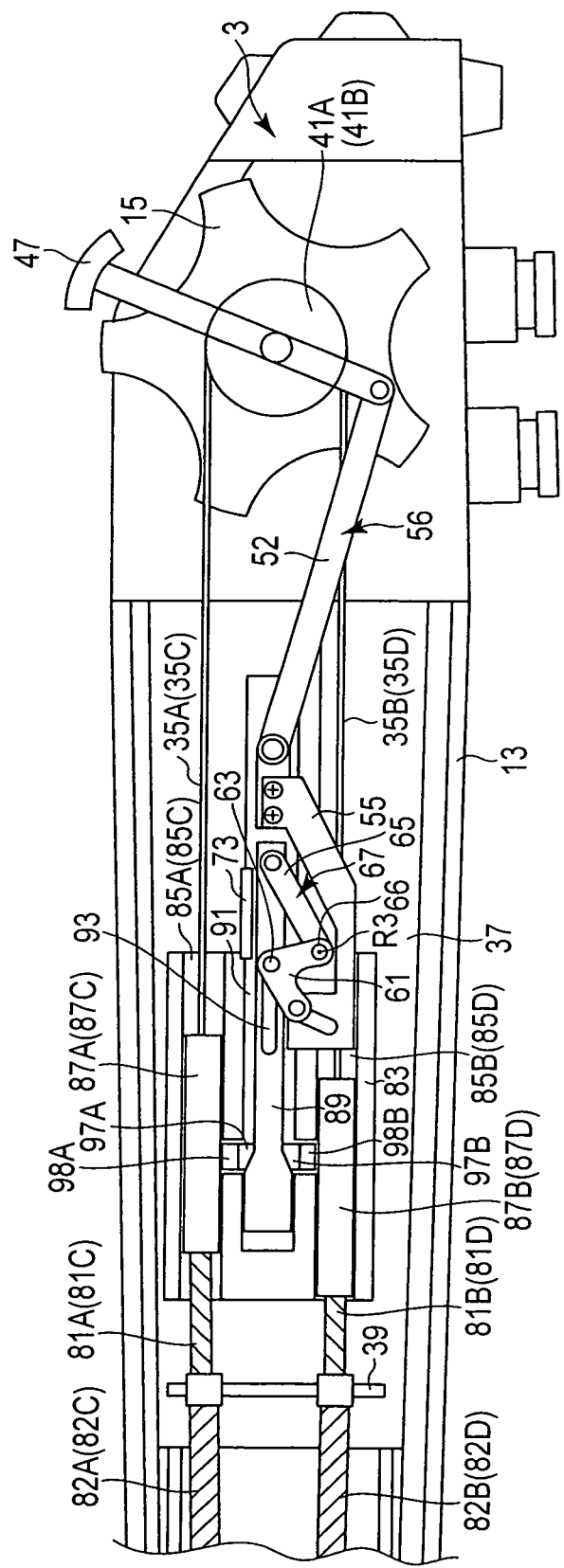
FIG. 14 is a schematic view showing an internal configuration of a holding case of a holding section in the endoscope according to the second embodiment.

FIG. 14 is a view showing an internal configuration of a holding case 13 of a holding section 3. As shown in FIG. 14, like the first embodiment, a substrate 37, a plate-shaped member 39, and pulleys 41A and 41B are provided in the holding case 13. Proximal ends of the bending operation wires 35A and 35B are fixed to the pulley 41A. Proximal ends of the bending operation wires 35C and 35D are fixed to the pulley 41B. Additionally, like the first embodiment, when the pulley 41A rotates in response to input of an operation through a bending operation knob 15, the bending operation wire 35A or the bending operation wire 35B is pulled. As a result, the first bending section 6 performs a bending motion in, e.g., up-and-down directions. Furthermore, when the pulley 41B rotates, the bending operation wire 35C or the bending operation wire 35D is pulled. As a result, the first bending section 6 performs the bending motion in, e.g., left-and-right directions.

Moreover, like the first embodiment, a second bending tube 21, a first reticular tube 25, and a first envelope 26 are sequentially arranged in the second bending section 7 from the inner peripheral direction side. Therefore, the second bending section 7 has flexibility. Thus, when an external force functions due to bending of the first bending section 6, the second bending section 7 is bent. That is, the second bending section 7 performs the bending motion to follow the bending motion of the first bending section 6. As described above, the second bending section 7 is an motion portion configured to carry out the bending motion in response to input of an operation through the bending operation knob 15. Further, the bending operation wires 35A to 35D are transmitting portions configured to transmit input of operations to the second bending section 7.

As shown in FIG. 14, proximal ends of the respective second coil pipes 82A to 82D are fixed to the plate-shaped member 39. The respective first coil pipes 81A to 81D are extended to the proximal direction side of the plate-shaped member 39. A columnar member 83 is fixed to the substrate 37. The columnar member 83 is placed to the proximal direction side of the plate-shaped member 39. Four groove portions 85A to 85D are formed in the columnar member 83 along the longitudinal axis C.

Further, four movable bodies 87A to 87D are provided in the holding case 13. The proximal end of the corresponding first coil pipe 81A to 81D is fixed to each of the movable bodies 87A to 87D. Each of the bending operation wires 35A to 35D is extended to the proximal direction side of the corresponding movable body 87A to 87D. The respective first coil pipes 81A to 81D move along the longitudinal axis C with respect to the holding case 13 in accordance with the bending motion of the second bending section 7. At this time, each of the movable bodies 87A to 87D move integrally with the corresponding first coil pipe 81A to 81D. That is, the respective movable bodies 87A to 87D serve as interlocking movement members configured to move along the longitudinal axis C with respect to the holding case 13 in tandem with the bending motion of the second bending section 7 which is the motion portion. Here, each of the movable members 87A to 87D moves in the corresponding groove portion 85A to 85D.

A switching operation lever 47 performs a switching operation of a state of the second bending section 7, which is the motion portion, between a movable state and a fixed state. In a state that the second bending section 7 is the movable state, when an acting force F1 is applied to the switching operation lever 47, the switching operation to the fixed state is carried out. In a state that the second bending section 7 is the fixed state, when acting force F'1, whose direction is opposite to that of the acting force F1, is applied to the switching operation lever 47, the switching operation to the movable state is carried out.

Figure 15:
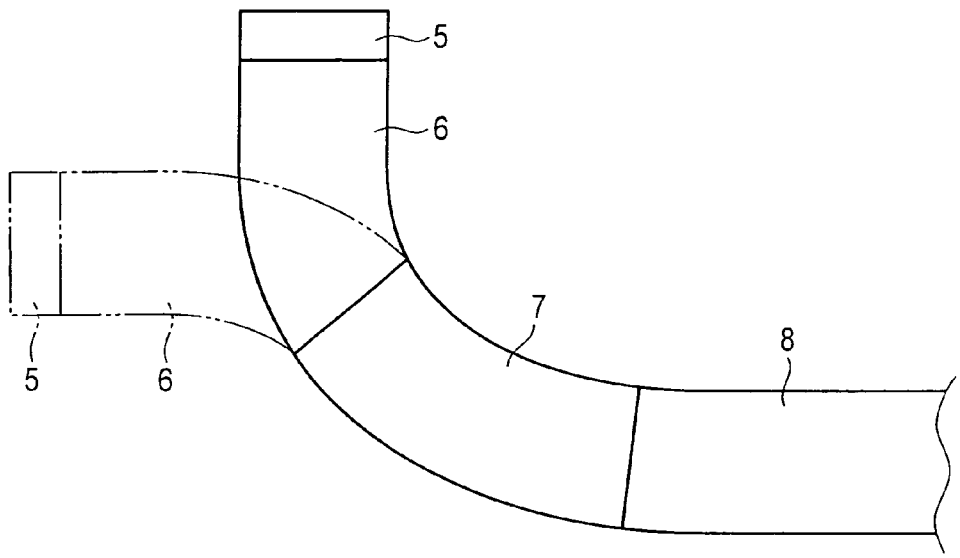
FIG. 15 is a schematic view showing motion states of the first bending section and the second bending section when the second bending section in the endoscope according to the second embodiment is a fixed state.

In a state that the second bending section 7 is the movable state, like the first embodiment, the first bending section 6 bends by input of an operation through a bending operation knob 15. Furthermore, the second bending section 7 performs the bending motion to follow the bending motion of the first bending section 6. FIG. 15 is a view showing motion states of the first bending section 6 and the second bending section 7 when the second bending section 7 is the fixed state. As shown in FIG. 15, when the second bending section 7 is the fixed state, the second bending section 7 is fixed and held irrespective of input of an operation through the bending operation knob 15, and it does not perform the bending motion. Therefore, the first bending section 6 alone performs the bending motion in response to input of an operation through the bending operation knob 15. Here, in this embodiment, differing from the first embodiment, even if the second bending section 7 is in a state excluding a straight state, the second bending section 7 can be fixed and held. Therefore, the second bending section 7 can be fixed and held in various bending states (which will be described later in detail).

Figure 16:
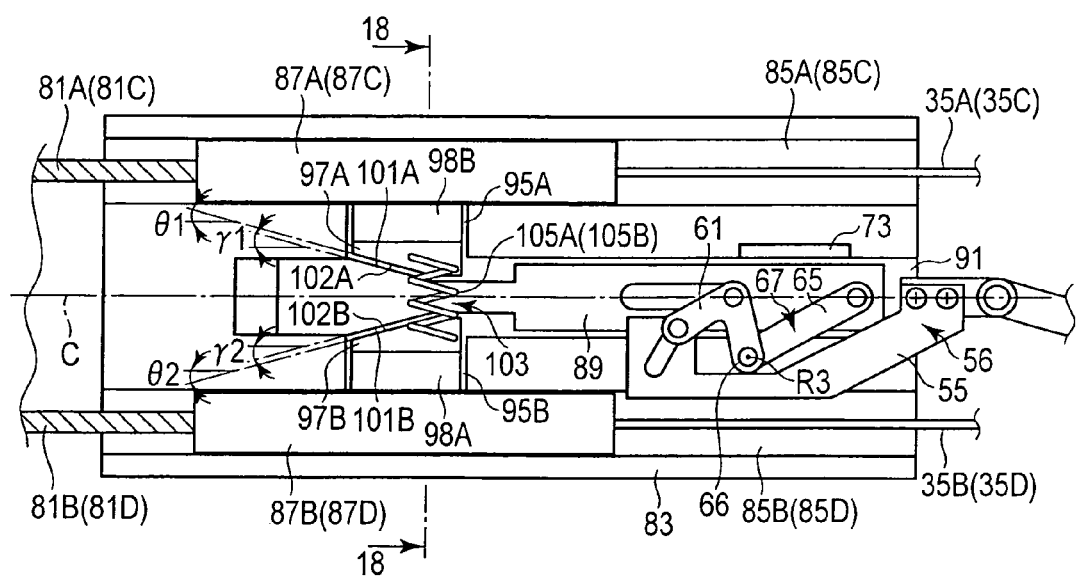
FIG. 16 is a schematic view showing a mechanism configured to transmit a switching operation of a switching operation lever when the second bending section in the endoscope according to the second embodiment is a movable state.
Figure 17:
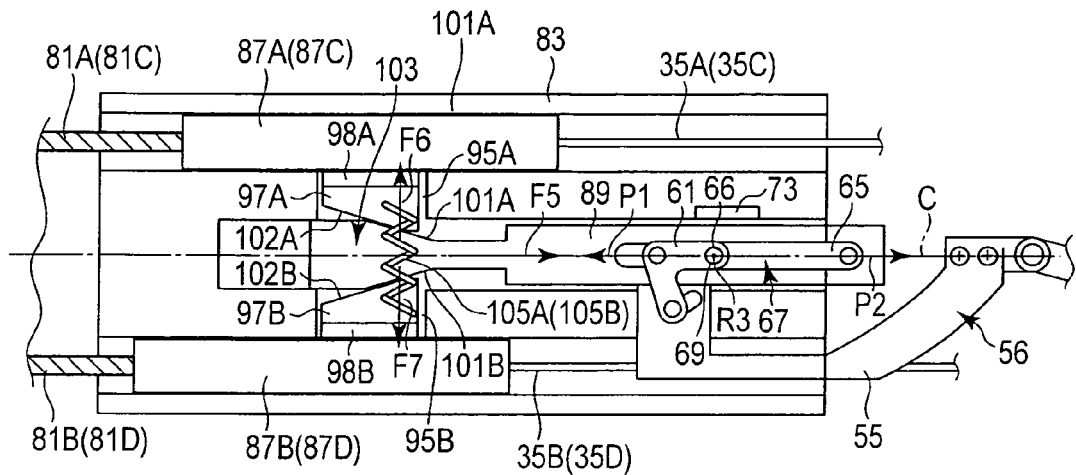
FIG. 17 is a schematic view showing the mechanism configured to transmit the switching operation of the switching operation lever when the second bending section in the endoscope according to the second embodiment is the fixed state.

FIG. 16 and FIG. 17 are views showing a mechanism configured to transmit the switching operation using the switching operation lever 47. Here, the second bending section 7 is the movable state in a state shown in FIG. 16, and the second bending section 7 is the fixed state in a state shown in FIG. 17. As shown in FIG. 16 and FIG. 17, like the first embodiment, a moving unit 56, a link unit 67, and a stopper member 73 are provided in the holding case 13. The moving unit 56 includes a slide member 52 and a plate-shaped member 55 like the first embodiment. Furthermore, the link unit 67 includes a first link 61 and a second link 65 like the first embodiment. Here, since the slide member 52, the plate-shaped member 55, the first link 61, the second link 65, and the stopper member 73 have the same configurations and functions as those in the first embodiment, a description thereof will be omitted.

As shown in FIG. 16 and FIG. 17, in this embodiment, a bar-shaped member 46 is not provided in the holding case 13. Instead, the moving unit 56 includes a slide member 89 configured to move along the longitudinal axis C in this embodiment. The slide member 89 is attached to the second link 65 of the link unit 67. As shown in FIG. 16, when the moving unit 56 is placed at a first movement position, the slide member 89 is placed at a first slide position. Moreover, as shown in FIG. 17, when the moving unit 56 is placed at a second movement position, the slide member 89 is placed at a second slide position. It is to be noted that a hole-shaped portion 91 is provided in the columnar member 83 along the longitudinal axis C. The slide member 89 moves in the hole-shaped portion 91 between the first slide position and the second slide position. Additionally, a slide hole 93 is formed in the slide member 89. When the slide member 89 moves, the slide hole 93 moves along the longitudinal axis C with respect to the shaft member 63.

As described above in the first embodiment, when the moving unit 56 is placed at the second movement position, the first link 61 and the second link 65 form a substantially linear shape at a link coupling position R3. In a state that the first link 61 and the second link 65 form the substantially linear shape, acting force P1 acts on the first link 61 in a direction away from the link coupling position R3. Further, acting force P2 acts on the second link 65 in a direction away from the link coupling position R3. At this time, the acting force P2 also acts on the slide member 89. The acting direction of the acting force P2 substantially coincides with the proximal direction, and the acting force P2 infinitely increases. Therefore, when the acting force P2 acts, the slide member 89 moves from the first slide position to the second slide position toward the proximal direction.

Figure 18:
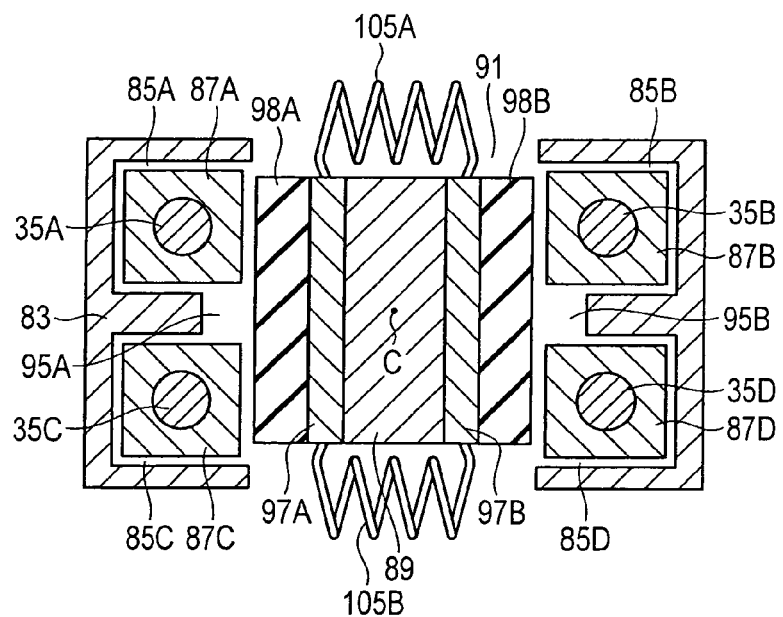
FIG. 18 is a cross-sectional view taken along a line 18-18 in FIG. 16.

FIG. 18 is a cross-sectional view taken along a line 18-18 in FIG. 16. As shown in FIG. 16 to FIG. 18, two communication grooves 95A and 95B are formed in the columnar member 83 along directions perpendicular to the longitudinal axis C. The communication groove 95A enables the hole-shaped portion 91 and the groove portions 85A and 85C to communicate with each other. Furthermore, the communication groove 95B enables the hole-shaped portion 91 and the groove portions 85B and 85D to communicate with each other. A brake caliper 97A and a brake pad 98A are arranged in the communication groove 95A. Moreover, a brake caliper 97B and a brake pad 98B are arranged in the communication groove 95B.

The slide member 89 moves to the second slide position when the acting force P2 acts. At this time, acting force (first acting force) F5 acts on the slide member (a first member) 89 in the proximal direction. When the slide member 89 moves to the second slide position, acting force (second acting force) F6 acts on the brake caliper (the second member) 97A from the slide member 89, and acting force (the second member) F7 acts on the brake caliper (the second member) 97B from the slide member 89. Each of the acting force F6 and the acting force F7 acts in the direction perpendicular to the longitudinal axis C. When the acting force F6 acts, the brake caliper 97A and the brake pad 98A move in the direction perpendicular to the longitudinal axis C. That is, the brake caliper 97A and the brake pad 98A move in a direction that is not parallel to the longitudinal axis C. As a result, the brake pad 98A comes into contact with the movable bodies 87A and 87C which are interlocking movement members. At this time, a regulating force acts on the movable bodies 87A and 87C from the brake pad 98A. The regulating force from the brake pad 98A enables the movable bodies 87A and 87C to be sandwiched between the brake pad 98A and the columnar member 83, and the movement of the movable bodies 87A and 87C along the longitudinal axis C is regulated.

Likewise, when the acting force F7 acts, the brake caliper 97B and the brake pad 98B move in the direction perpendicular to the longitudinal axis C. That is, the brake caliper 97B and the brake pad 98B move in a direction that is not parallel to the longitudinal axis C. As a result, the brake pad 98B comes into contact with the movable bodies 87B and 87D which are the interlocking movement members. At this time, the regulating force acts on the movable bodies 87B and 87D from the brake pad 98B. The regulating force from the brake pad 98B enables the movable bodies 87B and 87D to be sandwiched (held) between the brake pad 98B and the columnar member 83, and the movement of the movable bodies 87B and 87D along the longitudinal axis C is regulated. As described above, when the movement of each of the movable bodies 87A to 87D along the longitudinal axis C is regulated, shapes of the corresponding first coil pipe 81A to 81D is held between the distal end and the movable body 87A to 87D. When the shapes of the first coil pipes 81A to 81D are held, the second bending section 7 which is the motion portion is fixed and held.

Here, in this embodiment, the brake calipers 97A and 97B and the brake pads 98A and 98B serve as regulating portions configured to regulate the movement of the movable bodies 87A to 87D along the longitudinal axis C. Furthermore, the brake calipers 97A and 97B and the brake pads 98A and 98B function as abutting members configured to move in the direction that is not parallel to the longitudinal axis C (that is perpendicular to the longitudinal axis C) and configured to abut on the movable bodies 87A to 87D as interlocking movement members. In this embodiment, since the brake calipers 97A and 97B and the brake pads 98A and 98B move in the direction that is not parallel to the longitudinal axis C, the movement of the movable bodies 87A to 87D along the longitudinal axis C is regulated. Therefore, each of the movable bodies 87A to 87D can be held at any position as long as the movable bodies 87A to 87D are within a predetermined range in the direction parallel to the longitudinal axis C. Therefore, the second bending section 7 can be fixed and held in various bending states excluding the straight state.

As shown in FIG. 16, first inclined surfaces 101A and 101B inclined with respect to the longitudinal axis C are provided to the slide member 89. Each of a sharp angle (a first sharp angle) $\gamma 1$ between the first inclined surface 101A and the longitudinal axis C and a sharp angle (the first sharp angle) $\gamma 2$ between the first inclined surface 101B and the longitudinal axis C is smaller than 45°. Further, a second inclined surface 102A parallel to the first inclined surface 101A is provided to the brake caliper 97A. A sharp angle (a second sharp angle) $\theta 1$ between a second inclined surface 102A and the longitudinal axis C is smaller than 45°. Since acting force F6 perpendicular to the longitudinal axis C acts on the second inclined surface 102A from the first inclined surface 101A, the brake caliper 97A and the brake pad 98A move in the direction perpendicular to the longitudinal axis C. Here, since each of the sharp angle $\gamma 1$ and the sharp angle $\theta 1$ is smaller than 45°, the acting force F6 in the direction perpendicular to the longitudinal axis C is higher than acting force F5 whose direction is parallel to the longitudinal axis C.

Furthermore, a second inclined surface 102B parallel to the first inclined surface 101B is provided to the brake caliper 97B. A sharp angle (a second sharp angle) $\theta 2$ between the second inclined surface 102B and the longitudinal axis C is smaller than 45°. Since acting force F7 perpendicular to the longitudinal axis C acts on the second inclined surface 102B from the first inclined surface 101B, the brake caliper 97B and the brake pad 98B move in the direction perpendicular to the longitudinal axis C. Here, since each of the sharp angle $\gamma 2$ and the sharp angle $\theta 2$ is smaller than 45°, the acting force F7 in the direction perpendicular to the longitudinal axis C is higher than the acting force F5 in the direction parallel to the longitudinal axis C.

As described above, the slide member 89, the brake calipers 97A and 97B, and the brake pads 98A and 98B form a force amplifying unit 103 configured to amplify the acting forces (the second acting forces) F6 and F7 to be higher than the acting force (the first acting force) F5. When the acting force F6 is higher than the acting force F5, a regulating force that regulates the movement of the movable bodies 87A and 87C is amplified. Moreover, when the acting force F7 is higher than the acting force F5, a regulating force that regulates the movement of the movable bodies 87B and 87D is amplified.

Additionally, as described in the first embodiment, when the first link 61 and the second link 65 form the substantially linear shape, the acting force P1 and the acting force P2 infinitely increase. Therefore, the acting force P1 that infinitely increases acts on the first link 61 in the direction away from the link coupling position R3, and the acting force P2 that infinitely increases acts on the second link 65 in the direction away from the link coupling position R3. Therefore, the acting force P1 and the acting force P2 produced by a toggle section 69 enables holding the substantially linear shape at the link coupling position R3.

Further, in a state that the second bending section 7 which is the motion portion is fixed and held, a reaction force of a force that fixes and holds the second bending section 7 acts. Therefore, the reaction force of the regulating force acts on the slide member 89 from the movable bodies 87A to 87D, which are the interlocking movement members, through the brake calipers 97A and 97B and the brake pads 98A and 98B. Here, when the acting force P2 acts on the slide member 89, the slide member 89 moves in the proximal direction. Further, the regulating force acts on the movable bodies 87A and 87C from the brake pad 98A, and the regulating force acts on the movable bodies 87B and 87D from the brake pad 98B. Furthermore, the movement of the movable bodies 87A to 87D along the longitudinal axis C is regulated. Since the acting force P2 infinitely increases, the regulating force of the movable bodies 87A to 87D increases. When the regulating force increases, the movement of the movable bodies 87A to 87D along the longitudinal axis C is assuredly restricted, and the second bending section 7 is assuredly fixed and held.

Moreover, the acting force P2 infinitely increases, the reaction force of the regulating force from the movable bodies 87A to 87D is absorbed. Additionally, as described above, the acting force P1 and the acting force P2 hold the substantially linear shape at the link coupling position R3. Therefore, when the substantially linear shape is formed at the link coupling position R3, to avoid a change of the second bending section 7 to the movable state due to the reaction force of the regulating force, an operator does not have to constantly apply the acting force F1 to the switching operation lever 47. That is, even if the operator does not apply the acting force F1 to the switching operation lever 47, the state that the substantially linear shape is formed at the link coupling position R3 is held. Therefore, even if the operator does not apply the acting force F1 to the switching operation lever 47, the slide member 89 is placed and held at the second slide position. Therefore, at the time of fixing the second bending section 7, operability of, e.g., input of an operation of bending the first bending section 6 is improved. That is, at the time of fixing the second bending section 7, operability of operations other than fixing and holding the second bending section 7 is improved.

As shown in FIG. 16 to FIG. 18, spring members 105A and 105B are provided in the holding case 13. One end of each spring member 105A or 105B is connected to the brake caliper 97A, and the other end of the same is connected to the brake caliper 97B. In a state that the acting force F6 does not act, the brake caliper 97A and the brake pad a 98A are held at positions where they do not come into contact with the movable bodies 87A and 87C by a biasing force from the spring members 105A and 105B. At this time, since the brake pad 98A does not come into contact with the movable bodies 87A and 87C, the movable bodies 87A and 87C can move along the longitudinal axis C. Likewise, in a state that the acting force F7 does not act, the brake caliper 97B and the brake pad 98B are held at positions where they do not come into contact with the movable bodies 87B and 87D by the biasing force from the spring members 105A and 105B. At this time, since the brake pad 98B does not come into contact with the movable bodies 87B and 87D, the movable bodies 87B and 87D can move along the longitudinal axis C. Therefore, in a state that acting forces F6 and F7 do not act, the movable bodies 87A to 87D can move along the longitudinal axis C, and hence the second bending section 7 is the movable state.

Thus, in the endoscope 1 which is an insertion apparatus having the above-described configuration, in addition to the same effect as that of the first embodiment, the following effect can be exerted. That is, in the endoscope 1, when the brake calipers 97A and 97B and the brake pads 98A and 98B move in the direction that is not parallel to the longitudinal axis, the movement of the movable bodies 87A to 87D along the longitudinal axis C is regulated. Therefore, each of the respective movable bodies 87A to 87D can be placed and held at any position as long as this position is in a predetermined range. Therefore, the second bending section 7 can be fixed and held in various bent states excluding a straight state.

Moreover, the force amplifying unit 103 (the slide member 89, the brake calipers 97A and 97B, and the brake pads 98A and 98B) amplifies the acting forces (the second acting forces) F6 and F7 in the directions perpendicular to the longitudinal axis C to be higher than the acting force (the first acting force) F5 in the direction parallel to the longitudinal axis C. When the acting forces F6 and F7 are higher than the acting force F5, the regulating force of regulating the movement of the movable bodies 87A to 87D is amplified. As described above, the force amplifying unit 103 can further assuredly regulate the movement of the movable bodies 87A to 87D along the longitudinal axis C.

(Modification of Second Embodiment)

Figure 19:
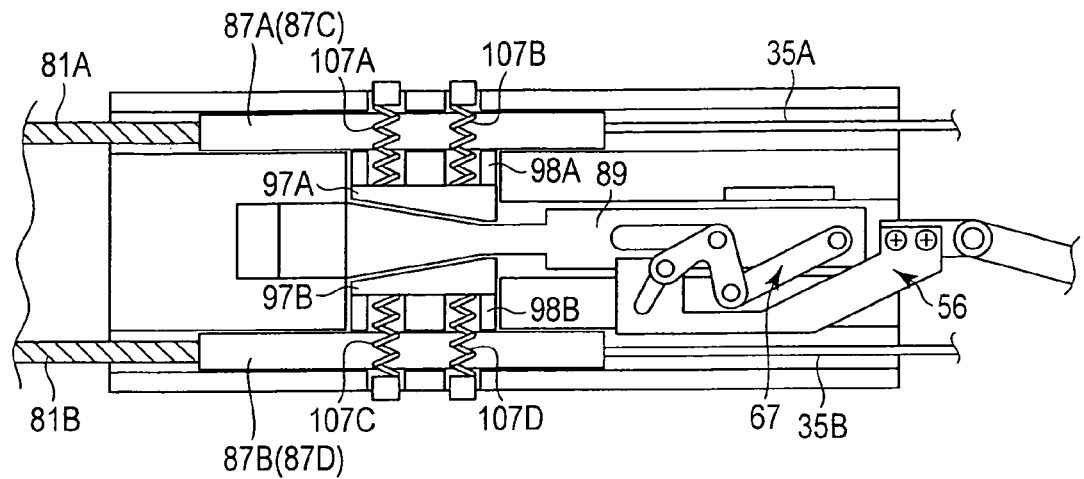
FIG. 19 is a schematic view showing a mechanism configured to transmit a switching operation of a switching operation lever in an endoscope according to a modification of the second embodiment.

Although the one end of each of the spring members 105A and 105B is connected to the brake caliper 97A and the other end of the same is connected to the brake caliper 97B in the second embodiment, the present invention is not restricted thereto. For example, as a modification, spring members 107A to 107D may be provided in place of the spring members 105A and 105B as shown in FIG. 19. One end of each spring member 107A and 107B is connected to the holding case 13, and the other end is connected to the brake caliper 97A. In a state that the acting force F6 does not act, the brake caliper 97A and the brake pad 98A are held at positions where they do not abut on the movable bodies 87A and 87C by a biasing force from the spring members 107A and 107B. Additionally, one end of each spring member 107C and 107D is connected to the holding case 13, and the other end of the same is connected to the brake caliper 97B. In a state that the acting force F7 does not act, the brake caliper 97B and the brake pad 98B are held at positions where they do not abut on the movable bodies 87B and 87D by a biasing force from the spring members 105C and 105D.

(Third Embodiment)

A third embodiment will now be described with reference to FIG. 20 to FIG. 24. It is to be noted that like reference numerals denote the same parts or parts having the same functions as those in the first embodiment and the second embodiment, and a description thereof will be omitted.

Figure 20:
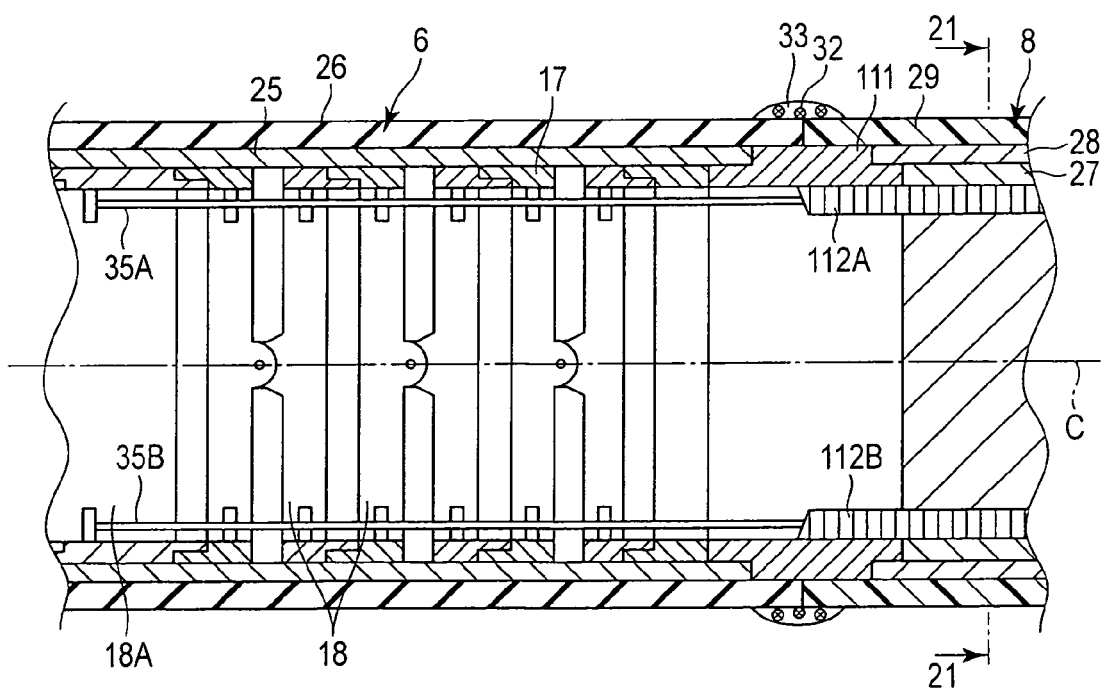
FIG. 20 is a cross-sectional view schematically showing a first bending section and a flexible tube section of an endoscope according to a third embodiment of the present invention.

In an endoscope 1 according to this embodiment, a second bending section 7 is not provided. FIG. 20 is a view showing configurations of a first bending section 6 and a flexible tube section 8. FIG. 21 is a cross-sectional view taken along a line 21-21 in FIG. 20. As shown in FIG. 20, in an insertion section 2 of the endoscope 1 which is an insertion apparatus according to this embodiment, a connection mouth ring 111 is provided between the first bending section 6 and the flexible tube section 8. A first bending tube 17 and a first reticular tube 25 are connected to a helical tube 27 and a second reticular tube 28 via the connection mouth ring 111. In the first bending section 6, like the first embodiment, distal ends of four bending operation wires 35A to 35D are connected to a first bending piece 18A that is placed on the most distal direction side in first bending pieces 18. Further, four coil pipes 112A to 112D are extended along the longitudinal axis C in the insertion section 2. Distal ends of the respective coil pipes 112A to 112D are fixed to the connection mouth ring 111 between the first bending section 6 and the flexible tube section 8. As shown in FIG. 21, each of the coil pipes 112A to 112D are arranged substantially 90° away from the neighboring coil pipes 112A to 112D around the longitudinal axis C. Each of the bending operation wires 35A to 35D are inserted through the corresponding coil pipe 112A to 112D.

FIG. 22 and FIG. 23 are views each showing an internal configuration of a holding case 13 of a holding section 3. Furthermore, FIG. 24 is a view showing configurations of a slide member 115 and brake calipers 125A and 125B. As shown in FIG. 22 and FIG. 23, in the holding case 13, like the second embodiment, a substrate 37, a plate-shaped member 39, pulleys 41A and 41B, and a columnar member 83 are provided. Proximal ends of the bending operation wires 35A and 35B are fixed to the pulley 41A. Proximal ends of the bending operation wires 35C and 35D are fixed to the pulley 41B. Moreover, like the first embodiment, when the pulley 41A rotates in response to input of an operation through a bending operation knob 15, the bending operation wire 35A or the bending operation wire 35B is pulled. As a result, the first bending section 6 carries out a bending motion in, e.g., up-and-down directions. Additionally, when the pulley 41B rotates, the bending operation wire 35C or the bending operation wire 35D is pulled. As a result, the first bending section 6 performs the bending motion in, e.g., left-and-right direction. As described above, the first bending section 6 serves as a motion portion configured to carry out the bending motion in response to input of an operation through the bending operation knob 15. Further, the bending operation wires 35A to 35D serve as transmitting portions configured to transmit input of an operation to the first bending section 6.

As shown in FIG. 22 and FIG. 23, the proximal ends of the respective coil pipes 112A to 112D are fixed to the plate-shaped member 39. The respective bending operation wires 35A to 35D are extended to the proximal direction side of the plate-shaped member 39. In a region to the proximal direction side of the plate-shaped member 39, a corresponding movable body 113A to 113D is fixed to outer peripheral portion of each of the bending operation wires 35A to 35D.

When the bending operation wires 35A to 35D are pulled and the first bending section 6 carries out the bending motion, the respective movable bodies 113A to 113D move along the longitudinal axis C with respect to the holding case 13 in tandem with the bending motion of the first bending section 6. At this time, each of the movable bodies 113A to 113D moves integrally with the corresponding bending operation wire 35A to 35D. That is, the respective movable bodies 113A to 113D are interlocking movement members configured to move along the longitudinal axis C with respect to the holding case 13 in tandem with the bending motion of the first bending section 6 which is the motion portion. Here, each of the respective movable bodies 113A to 113D moves in corresponding groove portion 85A to 85D formed in the columnar member 83.

A switching operation lever 47 performs a switching operation of a state of the first bending section 6 as the motion portion between a movable state and a fixed state. When the first bending section 6 is the movable state, applying acting force F1 to the switching operation lever 47 enables switching to the fixed state. Furthermore, when the second bending section 7 is the fixed state, applying acting force F'1, whose direction is opposite to that of the acting force F1, to the switching operation lever 47 enables switching the first bending section 6 to the movable state. When the first bending section 6 is the movable state, the first bending section 6 bends in response to input of an operation through the bending operation knob 15. On the other hand, when the first bending section 6 is the fixed state, the first bending section 6 is fixed and held irrespective of input of an operation through the bending operation knob 15, and it does not perform the bending motion.

Here, the first bending section 6 is the movable state in the state shown in FIG. 22, and the first bending section 6 is the fixed state in the state shown in FIG. 23. As shown in FIG. 22 and FIG. 23, in the holding case 13, like the first embodiment and the second embodiment, a moving unit 56 is provided. The moving unit 56 includes a slide member 52 like the first embodiment and the second embodiment. Furthermore, the moving unit 56 includes the slide member 115 attached to a slide member 52. The slide member 115 is movable along the longitudinal axis C. As shown in FIG. 22, when the moving unit 56 is placed at a first movement position, the slide member 115 is placed at a first slide position. Moreover, as shown in FIG. 23, when the moving unit 56 is placed at a second movement position, the slide member 115 is placed at a second slide position. The slide member 115 moves in a hole-shaped portion 91 between the first slide position and the second slide position.

The slide member 115 includes a link unit 117. Like the link unit 67 in the first embodiment, the link unit 117 includes a first link 121, a second link 122, and a coupling portion 123 that couples the first link 121 with the second link 122. The link unit 117 is attached to the slide member 115 through the coupling portion 123. Additionally, the coupling portion 123 forms a link coupling position R4 of the first link 121 and the second link 122. The first link 121 and the second link 122 pivotably move with each other about the link coupling position R4. When the slide member 115 moves along the longitudinal axis C, acting force F8 or acting force F'8, whose direction is opposite to that of the acting force F8, acts on the coupling portion 123.

As shown in FIG. 22, when the slide member 115 is placed at the first slide position, the first link 121 and the second link 122 form a substantially V-like shape having the link coupling position R4 as an apex (top). When the slide member 115 moves to the second slide position from this state, the acting force F8 acts on the coupling portion 123. As a result, the first link 121 and the second link 122 pivotally move with respect to each other about the link coupling position R4.

Additionally, as shown in FIG. 23, the first link 121 and the second link 122 form a substantially linear shape that does not bend at the link coupling position R4. In a state that the first link 121 and the second link 122 form the substantially linear shape, acting force P3 acts on the first link 121 in a direction away from the link coupling position R4. Further, acting force P4 acts on the second link 122 in a direction away from the link coupling position R4. In this embodiment, each of the acting force P3 and the acting force P4 act in a direction substantially perpendicular to the longitudinal axis C, and the acting force P3 and the acting force P4 have the same magnitude. Moreover, assuming that an angle formed between the first link 121 and the second link 122 at the link coupling position is $\alpha 3$ (see FIG. 24), the magnitude of the acting force P3 and the acting force P4 is proportionate to $\tan(\alpha 3/2)$. In a state that the substantially linear shape is formed, $\alpha 3$ is substantially 180°, and hence $\alpha 3/2$ is substantially 90°. Therefore, the acting force P3 and the acting force P4 infinitely increase. As described above, the link unit 117 includes a toggle section 119 configured to make the acting force P3 act on the first link 121 and make the acting force P4 act on the second link 122 in the direction away from the link coupling position R4.

As shown in FIG. 22 to FIG. 24, the brake caliper 125A and the brake pad 126A are arranged in a communication groove 95A of the columnar member 83. Further, the brake caliper 125B and the brake pad 126B are arranged in a communication groove 95B. As shown in FIG. 24, the brake caliper 125A is attached to the first link 121, and the brake caliper 125B is attached to the second link 122.

When the first link 121 and the second link 122 form the substantially linear shape at the link coupling position R4, the acting force P3 acts on the first link 121. When the acting force P3 acts, the brake caliper 125A and the brake pad 126A move in the direction perpendicular to the longitudinal axis C. That is, the brake caliper 125A and the brake pad 126A move in the direction that is not parallel to the longitudinal axis C. As a result, the brake pad 126A abuts on the movable bodies 113A and 113C which are the interlocking movement members. At this time, regulating force acts on the movable bodies 113A and 113C from the brake pad 126A. The regulating force from the brake pad 126A enables the movable bodies 113A and 113C to be held (sandwiched) between the brake pad 126A and the columnar member 83, and the movement of the movable bodies 113A and 113C along the longitudinal axis C is regulated.

Likewise, when the acting force P2 acts on the second link 122, the brake caliper 125B and the brake pad 126B move in the direction perpendicular to the longitudinal axis C. That is, the brake caliper 125B and the brake pad 126B move in the direction that is not parallel to the longitudinal axis C. As a result, the brake pad 126B abuts on the movable bodies 113B and 113D which are the interlocking movement members. At this time, a regulating force acts on the movable bodies 113B and 113D from the brake pad 126B. The regulating force from the brake pad 126B enables the movable bodies 113B and 113D to be held between the brake pad 126B and the columnar member 83, and the movement of the movable bodies 113B and 113D along the longitudinal axis C is regulated. As described above, when the movement of each of the movable bodies 113A to 113D along the longitudinal axis C is regulated, a shape of the corresponding bending operation wire 35A to 35D is held between the distal end and the movable body 113A to 113D. When the shapes of the bending operation wires 35A to 35D are held, the first bending section 6 which is the motion portion is fixed and held.

Here, in this embodiment, the brake calipers 125A and 125B and the brake pads 126A and 126B serve as regulating portions configured to regulate the movement of the movable bodies 113A to 113D along the longitudinal axis C. Moreover, the brake calipers 125A and 125B and the brake pads 12 function as abutting members configured to move in the direction that is not parallel to the longitudinal axis C (that is perpendicular to the longitudinal axis C) and abut on the movable bodies 113A to 113D which are the interlocking movement members. In this embodiment, when the brake calipers 125A and 125B and the brake pads 126A and 126B move in the direction that is not parallel to the longitudinal axis C, the movement of the movable bodies 113A to 113D along the longitudinal axis C is regulated. Therefore, each of the movable bodies 113A to 113D can be placed and held at any position as long as this position is in a predetermined range in the directions parallel to the longitudinal axis C. Thus, the first bending section 6 can be fixed and held in various bending states, excluding the straight state.

Here, as described above, when the first link 121 and the second link 122 form the substantially linear shape, the acting force P3 and the acting force P4 infinitely increase. Therefore, the acting force P3 that infinitely increases acts on the first link 121 in the direction away from the link coupling position R4, and the acting force P4 that infinitely increases acts on the second link 122 in the direction away from the link coupling position R4. Therefore, the acting force P3 and the acting force P4 generated by the toggle section 119 hold the substantially linear shape at the link coupling position R4.

Further, in a state that the first bending section 6, which is the motion portion, is fixed and held, a reaction force of a force that fixes and holds the first bending section 6 acts. Therefore, the reaction force of the regulating force acts on the link unit 117 from the movable bodies 113A to 113D, which are the interlocking movement members, through the brake calipers 125A and 125B and the brake pads 126A and 126B. Here, when the acting force P3 acts on the first link 121, the brake pad 126A moves in the direction perpendicular to the longitudinal axis C. Furthermore, the regulating force acts on the movable bodies 113A and 113C from the brake pad 126A. Furthermore, when the acting force P4 acts on the second link 122, the brake pad 126B moves in the direction perpendicular to the longitudinal axis C. The regulating force acts on the movable bodies 113B and 113D from the brake pad 126B. Moreover, the movement of the movable bodies 113A to 113D along the longitudinal axis C is regulated. Since the acting force P3 and the acting force P4 infinitely increase, the regulating force of the movable bodies 113A to 113D increases. When the regulating force increases, the movement of the movable bodies 113A to 113D along the longitudinal axis C is assuredly regulated, and the first bending section 6 is assuredly fixed and held.

Additionally, since the acting force P3 and the acting force P4 infinitely increase, the reaction force of the regulating force from the movable bodies 87A to 87D is absorbed. Further, as described above, the acting force P3 and the acting force P4 hold the substantially linear shape at the link coupling position R4. Therefore, when the substantially linear shape is formed at the link coupling position R4, to avoid the change of the first bending section 6 to the movable state caused due to the reaction force of the regulating force, an operator does not have to constantly apply the acting force F1 to the switching operation lever 47. That is, even if the operator does not apply the acting force F1 to the switching operation lever 47, the state that the substantially linear shape is formed at the link coupling position R4 is held. Therefore, at the time of the fixed state of the first bending section 6, operability of operations other than fixing and holding the first bending section 6 can be improved.

Furthermore, when the second bending section 7 is switched from the fixed state to the movable state by the switching operation using the switching operation lever 47, the slide member 115 moves to the first slide position from the second slide position. As a result, the acting force F'8 acts on the coupling portion 123 of the link unit 117, and the first link 121 and the second link 122 bend with respect to each other at the link coupling position R4. The acting force F'8 acts in the direction parallel to the longitudinal axis C, and this direction is different from a direction of the acting force P3 and a direction of the acting force P4. Therefore, even if the acting force F'8 is small, the first link 121 and the second link 122 can easily bend with respect to each other at the link coupling position R4. That is, even if the acting force F'1 applied by the operator using the switching operation lever 47 is small, the first link 121 and the second link 122 can easily bend with respect to each other at the link coupling position R4.

Moreover, since the first link 121 and the second link 122 bend with respect to each other at the link coupling position R4, the substantially linear shape is not formed at the link coupling position R4. Therefore, the acting force P3 and the acting force P4 that infinitely increase do not act on the link unit 117, and the reaction force of the regulating force from the movable bodies 113A to 113D is not absorbed. Therefore, the reaction force of the regulating fore changes the state of the link unit 117 to the state that first link 121 and the second link 122 form the substantially V-like shape at the link coupling position R4. As described above, even if the acting force F'1 applied by the operator using the switching operation lever 47 is small, the first bending section 6 can be easily switched to the movable state.

It is to be noted that, in this embodiment, the brake calipers 125A and 125B are attached to the link unit 117, differing from the second embodiment. Therefore, the first inclined surfaces 101A and 101B and the second inclined surfaces 102A and 102B provided in the second embodiment do not have to be provided. Additionally, the spring members 105A and 105B provided in the second embodiment do not have to be provided. Therefore, as compared with the second embodiment, the structure configured to restrict the movement of the movable bodies 113A to 113D (corresponding to the movable bodies 87A to 87D in the second embodiment) along the longitudinal axis C can be simplified and miniaturized.

Further, each of the movable bodies 113A to 113D is fixed the corresponding bending operation wire 35A to 35D without interposing any member therebetween. Therefore, when the movement of each of the movable bodies 113A to 113D along the longitudinal axis C is restricted, the shape of the corresponding bending operation wires 35A to 35D is further assuredly held. As a result, the first bending section 6 which is the motion portion is further assuredly fixed and held.

(Fourth Embodiment)

A fourth embodiment will now be described with reference to FIG. 25 and FIG. 26. It is to be noted that like reference numerals denote the same parts or parts having the same functions as those in the first embodiment to the third embodiment, and a description thereof will be omitted.

In this embodiment, a structure configured to regulate movement of movable bodies 113A to 113D along a longitudinal axis C is different from that of the third embodiment. FIG. 25 and FIG. 26 are views each showing an internal configuration of a holding case 13 of a holding section 3. Here, a first bending section 6 which is a motion portion is a movable state in a state shown in FIG. 25, and the first bending section 6 is the fixed state in a state shown in FIG. 26. As shown in FIG. 25 and FIG. 26, in this embodiment, a switching operation lever 47 is formed into a substantially L-like shape. Furthermore, a link unit 131 is attached to a second lever end 49B of the switching operation lever 47. In the switching operation lever 47, like the first embodiment, a dimension A1 between a pivoting axis R1 and a first lever end 49A is larger than a dimension A2 between the pivoting axis R1 and the second lever end 49B. Therefore, acting forces (second acting forces) F2 and F'2 acting on the link unit (a second member) 131 from the switching operation lever (a first member) 47 are higher than acting forces (first acting forces) F1 and F'1 acting on the switching operation lever (the first member) 47. As described above, a force amplifying unit 132 configured to amplify the acting forces (the second acting forces) F2 and F'2 to be higher than the acting forces (the first acting forces) F1 and F'1 is provided.

Like the link unit 67 in the first embodiment, the link unit 131 includes a first link 133 attached to the switching operation lever 47, a second link 135, and a coupling portion 137 that couples the first link 133 with the second link 135. The coupling portion 137 forms a link coupling position R5 of the first link 133 and the second link 135. The first link 133 and the second link 135 pivotably move with respect to each other about the link coupling position R5. The acting force F2 or the acting force F'2 acts on the first link 133 of the link unit 131 by a switching operation using the switching operation lever 47. As a result, the first link 133 pivotally moves, and acting force F9 or acting force F'9, whose direction is opposite to that of the acting force F9, acts on the coupling portion 137.

Figure 25:
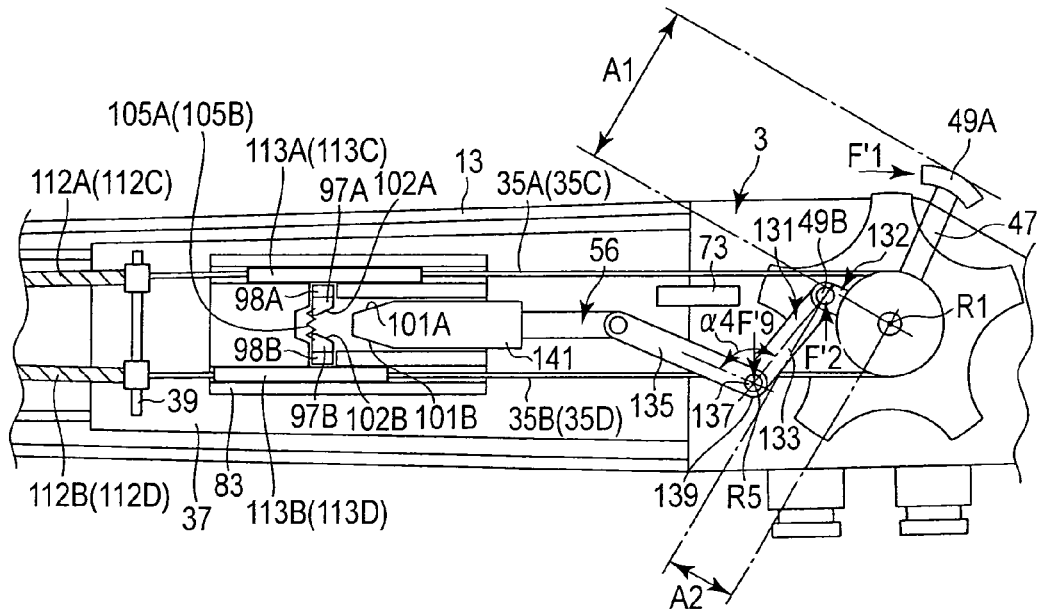
FIG. 25 is a schematic view showing an internal configuration of a holding case when a first bending section in an endoscope according to a fourth embodiment of the present invention is a movable state.

As shown in FIG. 25, when the first bending section 6 is the movable state, the first link 133 and the second link 135 form a substantially V-like shape having the link coupling position R5 as an apex (top). When the switching operation is performed from this state to the fixed state, the acting force F2 acts on the first link 133. Further, the first link 133 pivotally moves, and the acting force F9 acts on the coupling portion 137. As a result, the first link 133 and the second link 135 pivotally move with respect to each other about the link coupling position R5.

Figure 26:
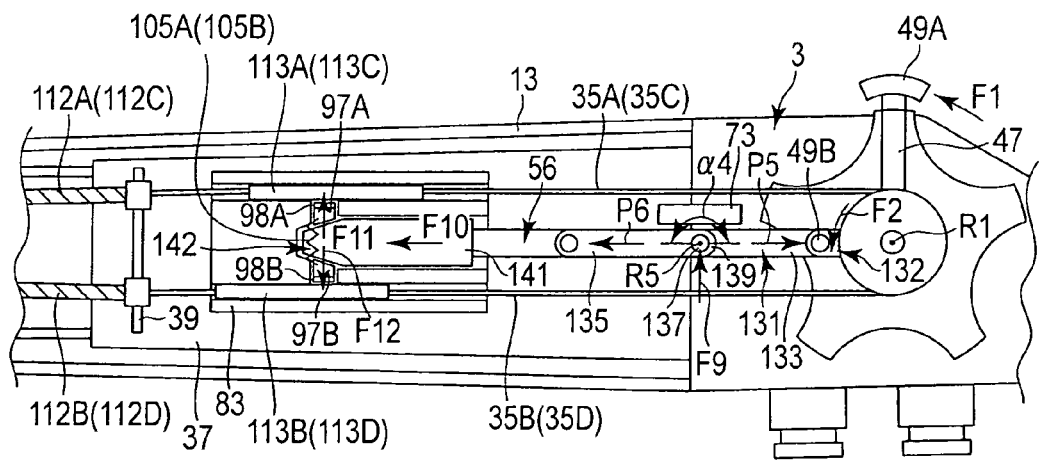
FIG. 26 is a schematic view showing the internal configuration of the holding case when the first bending section in the endoscope according to the fourth embodiment is a fixed state.

Furthermore, as shown in FIG. 26, the first link 133 and the second link 135 form a substantially linear shape that does not bend at the link coupling position R5. When the first link 133 and the second link 135 form the substantially linear shape, the acting force P5 acts on the first link 133 in a direction away from the link coupling position R5. Moreover, the acting force P6 acts on the second link 135 in the direction away from the link coupling position R5. Here, assuming that an angle formed between the first link 133 and the second link 134 at the link coupling position R5 is $\alpha 4$, magnitudes of the acting force P5 and the acting force P6 are proportionate to $\tan(\alpha 4/2)$. Since $\alpha 4$ is substantially 180° in the state that the substantially linear shape is formed, $\alpha 4/2$ is substantially 90°. Therefore, the acting force P5 and the acting force P6 infinitely increase. As described above, the link unit 131 includes a toggle section 139 configured to enable the acting force P5 to act on the first link 133 and enable the acting force P6 to act on the second link 135 in the direction away from the link coupling position R5 when the substantially linear shape is formed.

As shown in FIG. 25 and FIG. 26, a moving unit 56 is attached to the second link 135. The moving unit 56 includes a slide member 141 that moves along the longitudinal axis C. The slide member 141 is attached to the second link 135 of the link unit 131. As shown in FIG. 25, when the first bending section 6 is the movable state, the slide member 141 is placed at a first slide position. Moreover, as shown in FIG. 26, when the first bending section 6 is the fixed state, the slide member 141 is placed at a second slide position. The slide member 141 moves in a hole-shaped portion 91 provided in a columnar member 83 between the first slide position and the second slide position.

As described above, when the switching operation to the fixed state has been carried out, the first link 133 and the second link 135 form the substantially linear shape that does not bend at the link coupling position R5. Additionally, in a state that the first link 133 and the second link 135 form the substantially linear shape, the acting force P5 acts on the first link 133 in the direction away from the link coupling position R5. Further, the acting force P6 acts on the second link 135 in the direction away from the link coupling position R5. At this time, the acting force P6 also acts on the slide member 141. An acting direction of the acting force P6 substantially coincides with a distal direction, and the acting force P6 infinitely increases. Therefore, when the acting force P6 acts, the slide member 141 moves from the first slide position to the second slide position toward the distal direction.

The slide member 141 moves to the second slide position when the acting force P6 acts. At this time, acting force (the first acting force) F10 acts on the slide member (the first member) 141 in the distal direction. When the slide member 141 moves to the second slide position, acting force (the second acting force) F11 acts on the brake caliper (the second member) 97A from the slide member 141, and acting force (the second acting force) F12 acts on the brake caliper (the second member) 97B from the slide member 141. The acting force F11 and the acting force F12 act in the directions perpendicular to the longitudinal axis C. When the acting force F11 acts, the brake caliper 97A and the brake pad 98A move in the direction perpendicular to the longitudinal axis C. That is, the brake caliper 97A and the brake pad 98A move in the direction that is not parallel to the longitudinal axis C. As a result, the brake pad 98A abuts on movable bodies 113A and 113C which are interlocking movement members. At this time, a regulating force acts on the movable bodies 113A and 113C from the brake pad 98A. The regulating force from the brake pad 98A enables the movable bodies 113A and 113C to be held between the brake pad 98A and the columnar member 83, and the movement of the movable bodies 113A and 113C along the longitudinal axis C is regulated.

Likewise, when the acting force F12 acts, the brake caliper 97B and the brake pad 98B move in the direction perpendicular to the longitudinal axis C. That is, the brake caliper 97B and the brake pad 98B move in the direction that is not parallel to the longitudinal axis C. As a result, the brake pad 98B abuts on movable bodies 113B and 113D as the interlocking movement members. At this time, the regulating force acts on the movable bodies 113B and 113D from the brake pad 98B. The regulating force from the brake pad 98B enables the movable bodies 113B and 113D to be held between the brake pad 98B and the columnar member 83, and the movement of the movable bodies 113B and 113D along the longitudinal axis C is regulated. As described above, when the movement of each of the respective movable bodies 113A to 113D along the longitudinal axis C is regulated, a shape of corresponding bending operation wire 35A to 35D is held between the distal end and the movable body 113A to 113D. When the shapes of the bending operation wires 35A to 35D are held, the first bending section 6 which is the motion portion is fixed and held.

Further, like the slide member 89 in the second embodiment, first inclined surfaces 101A and 101B are provided to the slide member 141. Furthermore, like the second embodiment, a second inclined surface 102A is provided to the brake caliper 97A, and a second inclined surface 102B is provided to the brake caliper 97B. Therefore, the slide member 141, the brake calipers 97A and 97B, and the brake pads 98A and 98B form a force amplifying unit 142 configured to amplify the acting forces (the second acting forces) F11 and F12 to be higher than the acting force (the first acting force) F10. When the acting force F11 is higher than the acting force F10, the regulating force that regulates the movement of the movable bodies 113A and 113C is amplified. Moreover, when the acting force F12 is higher than the acting force F10, the regulating force that regulates the movement of the movable bodies 113B and 113D is amplified.

Additionally, as described above, when the first link 133 and the second link 135 form the substantially linear shape, the acting force P5 and the acting force P6 infinitely increase. Therefore, the acting force P5 that infinitely increases acts on the first link 133 in the direction away from the link coupling position R5, and the acting force P6 that infinitely increases acts on the second link 135 in the direction away from the link coupling position R5. Therefore, the acting force P5 and the acting force P6 produced by the toggle section 139 hold the substantially linear shape at the link coupling position R5.

Further, in the state that the first bending section 6 as the motion portion is fixed and held, a reaction force of a force that fixes and holds the first bending section 6 acts. Therefore, the reaction force of the regulating force acts on the slide member 141 from the movable bodies 113A to 113D as the interlocking movement members through the brake calipers 97A and 97B and the brake pads 98A and 98B. Here, when the acting force P6 acts on the slide member 141, the slide member 141 moves in the distal direction. Furthermore, the regulating force acts on the movable bodies 113A and 113C from the brake pad 98A, and the regulating force acts on the movable bodies 113B and 113D from the brake pad 98B. Moreover, the movement of the movable bodies 113A to 113D along the longitudinal axis C is regulated. Since the acting force P6 infinitely increases, the regulating force of the movable bodies 113A to 113D increases. When the regulating force increases, the movement of the movable bodies 113A to 113D along the longitudinal axis C is assuredly regulated, and the first bending section 6 is securely fixed and held.

Additionally, since the acting force P6 infinitely increases, the reaction force of the regulating force from the movable bodies 113A to 113D is absorbed. Further, as described above, the acting force P5 and the acting force P6 hold the substantially linear shape at the link coupling position R5. Therefore, when the substantially linear shape is formed at the link coupling position R5, to avoid the change of the first bending section 6 to the movable state caused due to the reaction force of the regulating force, an operator does not have to constantly apply the acting force F1 to the switching operation lever 47. That is, even if the operator does not apply the acting force F1 to the switching operation lever 47, the state that the substantially linear shape is formed at the link coupling position R5 is held. Therefore, even if the operator does not apply the acting force F1 to the switching operation lever 47, the slide member 141 is positioned and held at the second slide position. Therefore, when the first bending section 6 is the fixed state, operability of operations other than fixing and holding the first bending section 6 can be improved.

Further, in the holding case 13, like the first embodiment, a stopper member 73 is provided. When the link unit 131 has changed from the state that the substantially V-like shape having an angle (a first angle) α4 smaller than 180° is formed at the link coupling position R5 to the state that the substantially linear shape is formed at the link coupling position R5, the link unit 131 abuts on the stopper member 73 at the link coupling position R5. When the link unit 131 abuts on the stopper member 73 at the link coupling position R5, it is possible to avoid the change of the link unit 131 to a state that an inverted V-like shape having an angle α4 larger than 180° is formed at the link coupling position R5. As a result, the link unit 131 is more assuredly held in the state that the substantially linear shape is formed at the link coupling position R5. When the substantially linear shape is held, the acting force P5 that infinitely increases acts on the first link 133, and the acting force P6 that infinitely increases acts on the second link 135. As a result, the slide member 141 is more assuredly held at the second slide position. Therefore, the sufficiently high regulating force regulates the movement of the movable bodies 113A to 113D along the longitudinal axis C.

Moreover, when the first bending section 6 has been switched to the movable state from the fixed state by the switching operation using the switching operation lever 47, the acting force F'2 acts on the first link 133, and the first link 133 pivotally moves. As a result, the acting force F'9 acts on the coupling portion 137 of the link unit 131, and the first link 133 and the second link 135 bend with respect to each other at the link coupling position R5. A direction of the acting force F'9 is different from a direction of the acting force P5 and a direction of the acting force P6. Therefore, even if the acting force F'9 is small, the first link 133 and the second link 135 can easily bend with respect to each other at the link coupling position R5. That is, even if the acting force F'1 applied by an operator using the switching operation lever 47 is small, the first link 133 and the second link 135 can easily bend with respect to each other at the link coupling position R5.

Furthermore, when the first link 133 and the second link 135 bend with respect to each other at the link coupling position R5, the substantially linear shape is not formed at the link coupling position R5. Therefore, the acting force P5 and the acting force P6 that infinitely increase do not act on the link unit 131, and the reaction force of the regulating force from the movable bodies 113A to 113D is not absorbed. Therefore, the reaction force of the regulating force changes the state of the link unit 131 to the state that the first link 133 and the second link 135 form the substantially V-like shape at the link coupling position R5. As a result, the slide member 141 moves from the second slide position to the first slide position.

Additionally, like the second embodiment, spring members 105A and 105B are provided in the holding case 13. When the slide member 141 is placed at the first slide position, the acting force F11 and the acting force F12 do not act. When the acting force F11 does not act, the brake caliper 97A and the brake pad 98A are held at positions where they do not abut on the movable bodies 113A and 113C by biasing forces from the spring members 105A and 105B. At this time, since the brake pad 98A does not abut on the movable bodies 113A and 113C, the movable bodies 113A and 113C can move along the longitudinal axis C. Likewise, when the acting force F12 does not act, the brake caliper 97B and the brake pad 98B are held at positions where they do not abut on the movable bodies 113B and 113D by the biasing forces from the spring members 105A and 105B. At this time, since the brake pad 98B does not abut on the movable bodies 113B and 113D, the movable bodies 113B and 113D can move along the longitudinal axis C. Therefore, when the acting forces F11 and F12 do not act, the movable bodies 113A to 113D can move along the longitudinal axis C, and hence the first bending section 6 is the movable state.

It is to be noted that, in this embodiment, the link unit 131 is attached to the switching operation lever 47 without interposing any member therebetween as different from the second embodiment. Therefore, differing from the second embodiment, a slide member 52 and a plate-shaped member 55 are not provided. That is, the link unit 131, the slide member 141, the brake calipers 97A and 97B, and the brake pads 98A and 98B regulate the movement of the movable bodies 113A to 113D along the longitudinal axis C. Therefore, as compared with the second embodiment, the structure configured to regulate the movement of the movable bodies 113A to 113D (corresponding to the movable bodies 87A to 87D in the second embodiment) along the longitudinal axis C can be simplified and miniaturized.

(Modification of Fourth Embodiment)

Here, a modification of the fourth embodiment will now be described with reference to FIG. 27 and FIG. 28. It is to be noted that a first bending section 6 which is a motion portion is a movable state in a state shown in FIG. 27, and the first bending section 6 is a fixed state in a state shown in FIG. 28. As shown in FIG. 27 and FIG. 28, in this modification, differing from the fourth embodiment, the first inclined surfaces 101A and 101B and the second inclined surfaces 102A and 102B are not provided. Instead, the link unit 117 described in the third embodiment is attached to a slide member 141. The link unit 117 is attached to a slide member 115 at a link coupling position R4 between a first link 121 and a second link 122. Like the third embodiment, a brake caliper 125A and a brake pad 126A are attached to the first link 121.

Further, a brake caliper 125B and a brake pad 126B are attached to the second link 122.

When the slide member 141 moves to a second slide position, the first link 121 and the second link 122 form a substantially linear shape at the link coupling position R4. Furthermore, acting force P3 acts on the first link 121, and acting force P4 acts on the second link 122. It is to be noted that particulars of configurations and functions of the link unit 117, the brake calipers 125A and 125B, and the brake pads 126A and 126B are the same as those in the third embodiment, and hence a description thereof will be omitted.

In this modification, the two link units 117 and 131 are provided to a configuration which regulates the movement of movable bodies 113A to 113D along a longitudinal axis C. When the first bending section 6 is the fixed state, the acting forces P3 and P4 that infinitely increase act on the link unit 117. Furthermore, acting forces P5 and P6 that infinitely increase act on the link unit 131. Therefore, since the link unit 117 on which the acting forces P3 and P4 act and the link unit 131 on which the acting forces P5 and P6 act are provided, a regulating force that regulates the movement of the movable bodies 113A to 113D increases. As a result, the movement of the movable bodies 113A to 113D is further assuredly regulated, and the first bending section 6 is further securely fixed and held.

(Fifth Embodiment)

A fifth embodiment will now be described with reference to FIG. 29 to FIG. 31. It is to be noted that like reference numerals denote the same parts or parts having the same functions as those in the first embodiment to the fourth embodiment, and a description thereof will be omitted.

In an endoscope 1 according to this embodiment, a second bending section 7 is not provided. FIG. 29 is a view showing a configuration of a distal hard section 5. As shown in FIG. 29, in an insertion section 2, a treatment tool channel 151 is extended to the distal hard section 5 along a longitudinal axis C. In the distal hard section 5, a hollow portion 152 communicating with the treatment tool channel 151 is provided. The hollow portion 152 is opened toward a direction perpendicular to the longitudinal axis C in an opening portion 153. A treatment tool raiser 155 is provided in the hollow portion 152. The treatment tool raiser 155 is disposed so that it pivotably moves about a shaft member 156. The treatment tool raiser 155 pivotally moves between a first raiser position (a position indicated by a solid line in FIG. 29) and a second raiser position (a position indicated by a dotted line in FIG. 29). When the treatment tool raiser 155 pivotally moves to the second raiser position, a distal end portion of a treatment tool 157, inserted through the treatment tool channel 151, bends in the direction perpendicular to the longitudinal axis C. Further, the distal end portion of the treatment tool 157 is held (sandwiched) between the treatment tool raiser 155 and the distal hard section 5, and the distal end portion of the treatment tool 157 is fixed and held in a bent state.

Furthermore, in the insertion section 2, a raising wire 159 is provided along the longitudinal axis C. A distal end of the raising wire 159 is connected to the treatment tool raiser 155. FIG. 30 and FIG. 31 are views each showing an internal configuration of a holding case 13 of a holding section 3. As shown in FIG. 30 and FIG. 31, in the holding case 13, like the first embodiment, a bar-shaped member 46, a moving unit 56, and a link unit 67 are provided. A proximal end of the raising wire 159 is connected to the bar-shaped member 46. The raising wire 159 is pulled in response to input of an operation (a switching operation) through a switching operation lever 47. That is, the raising wire 159 moves along the longitudinal axis C. As a result, the treatment tool raiser 155 pivotally moves, and it moves to the second raiser position.

As described above, the treatment tool raiser 155 functions as a motion portion configured to perform a pivoting motion in response to input of an operation through the switching operation lever 47. Furthermore, the raising wire 159 is a transmitting portion configured to transmit input of an operation to the treatment tool raiser 155. Moreover, the raising wire 159 is an interlocking movement member configured to moves along the longitudinal axis C with respect to the holding case 13 in tandem with the pivoting motion of the treatment tool raiser 155 which is the motion portion.

Additionally, the switching operation lever 47 carries out a switching operation of a state of the treatment tool raiser 155, which is the motion portion, between a movable state and a fixed state. In the movable state, the treatment tool raiser 155 can pivotally move between the first raiser position and the second raiser position. In the fixed state, the treatment tool raiser 155 is fixed and held at the second raiser position.

Figure 31:
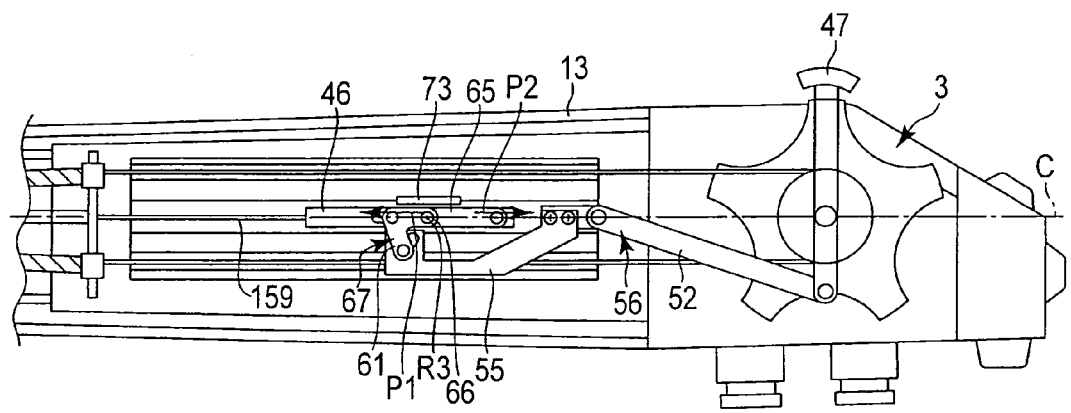
FIG. 31 is a schematic view showing the internal configuration of the holding case when the treatment tool raiser the endoscope according to the fifth embodiment is a fixed state.

Here, the treatment tool raiser 155 is the movable state in a state shown in FIG. 30, and the treatment tool raiser 155 is the fixed state in a state shown in FIG. 31. As shown in FIG. 30 and FIG. 31, when the treatment tool raiser 155 has been switched from the movable state to the fixed state by the switching operation, the moving unit 56 moves from a first movement position to a second movement position. As a result, a first link 61 and a second link 65 form a substantially linear shape at a link coupling position R3 of the link unit 67, and acting forces P1 and P2 that infinitely increase act on the link unit 67. The acting force P2 also acts on the bar-shaped member 46. As a result, the bar-shaped member 46 moves in the proximal direction.

When the bar-shaped member 46 moves, a pulling force which is regulating force acts on the raising wire 159. As a result, the raising wire 159 is pulled in the proximal direction. When the raising wire 159 is pulled, the raising wire 159 is held in a tensed state, and the movement of the raising wire 159 along the longitudinal axis C is regulated. That is, the bar-shaped member 46 serves as a regulating portion configured to regulate the movement of the raising wire 159 along the longitudinal axis C. When the raising wire 159 is held in the pulled state, the treatment tool raiser 155 is the fixed state.

It is to be noted that detailed configurations and functions of the bar-shaped member 46, the moving unit 56, and the link unit 67 are the same as those in the first embodiment, and hence a description thereof will be omitted.

Moreover, as described above in this embodiment, the link unit 67 on which the acting forces P1 and P2 that infinitely increase act can be also used for a structure that fixes and holds motion portions other than the bending sections (the first bending section 6, a second bending section 7) of the endoscope 1. That is, a structure that fixes and holds the motion portions (6, 7, 55) provided at the distal end portion of the insertion section 2 can suffice.

(Other Modifications)

Figure 32:
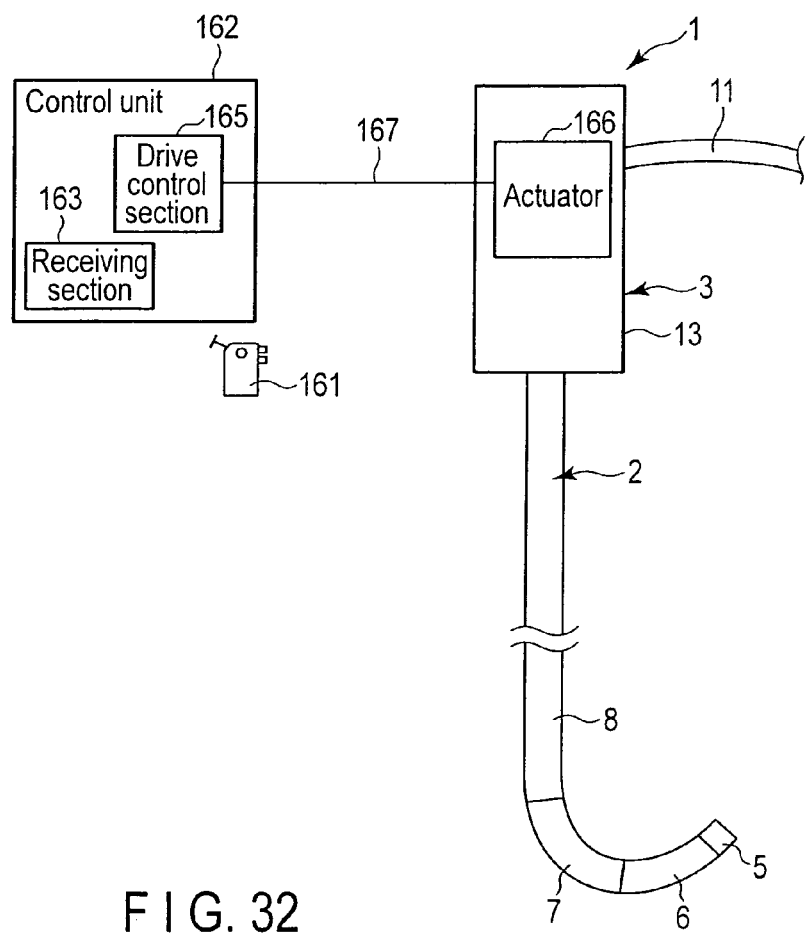
FIG. 32 is a schematic view showing an endoscope according to a modification of the first to fifth embodiments.

Although the switching operation lever 47 performs the switching operation of the motion portion (6, 7, 55) between the movable state and the fixed state in the foregoing embodiments, the present invention is not restricted thereto. For example, as a modification shown in FIG. 32, a wireless remote controller (a switching operating section) 161 may be used to switch a second bending section 7 that is a motion portion. In this modification, like the second embodiment, a moving unit 56, a link unit 67, brake calipers 97A and 97B, and brake pads 98A and 98B are provided in a holding case 13.

Further, in this modification, a control unit 162 is provided outside the holding case 13. The control unit 162 includes a receiving section 163 configured to receive a switching operation using the wireless remote controller 161, and a drive control section 165. An actuator 166 is provided in the holding case 13. The drive control section 165 is electrically connected to the actuator 166 through an electrical signal line 167.

When the second bending section 7 has been switched from the movable state to the fixed state by the wireless remote controller 161, the drive control section 165 controls to drive the actuator 166. When the actuator 166 is controlled to be driven, a slide member 89 moves from a first slide position to a second slide position through a slide member 52, a plate-shaped member 55, and a link unit 67. Since motions of the slide member 52, the plate-shaped member 55, and the link unit 67 are the same as those in the second embodiment, a description will be omitted. When the slide member 89 moves to the second slide position, a brake pad 98A regulates movement of movable bodies 87A and 87C, and a brake pad 98B regulates movement of movable bodies 87B and 87D.

Moreover, although the movement of each of the movable bodies 113A to 113D fixed to the corresponding bending operation wire 35A to 35D is regulated in the third embodiment, the present invention is not restricted thereto. For example, the link unit 117 and the brake pads 126A and 126B in the third embodiment may be used to regulate the movement of the movable bodies 87A to 87D in the second embodiment. In this case, like the second embodiment, the second bending section 7 is fixed and held.

Additionally, although the motion portion (6, 7, 55) provided in the insertion section 2 of the endoscope 1 are fixed and held in the foregoing embodiments, the present invention is not restricted thereto. For example, the configuration of each foregoing embodiment may be used to fix and hold the bending section provided to an insertion section of a treatment tool configured to be inserted into a body cavity. That is, a configuration suffices which fixes and holds a motion portion of an insertion apparatus including an insertion section inserted into, e.g., a body cavity or a pipe.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion apparatus comprising:
   an insertion section which includes a motion portion at a distal end portion thereof, and which is extended along a longitudinal axis;
   a holding section which is provided to a proximal direction side of the insertion section;
   a transmitting portion configured to transmit, to the motion portion, input of an operation of performing a motion in the motion portion;
   an interlocking movement member configured to move along the longitudinal axis with respect to the holding section in tandem with the motion of the motion portion;
   a switching operating section which is configured to perform a switching operation of a state of the motion portion between a state that the motion portion performs the motion in response to the input of the operation and a state that the motion of the motion portion is regulated irrespective of the input of the operation;
   a moving unit which is configured to move in accordance with the switching operation between a first movement position in the state that the motion portion performs the motion and a second movement position in the state that the motion of the motion portion is regulated;
   a link unit including: a first link; a second link which is attached to the first link at a link coupling position; and a coupling portion which couples the first link with the second link to allow their pivotal movement with respect to each other about the link coupling position in a state that the first link and the second link form a substantially V-like shape having the link coupling position as an apex when the moving unit is placed at the first movement position and in a state that the first link and the second link form a substantially linear shape that does not bend at the link coupling position when the moving unit is placed at the second movement position; and
   a regulating portion which configured to regulate movement of the interlocking movement member along the longitudinal axis, and configured to fix and hold the motion portion when the first link and the second link of the link unit form the substantially linear shape.

2. The insertion apparatus according to claim 1,
   wherein the link unit includes a toggle section which is configured to make acting force, which increases a regulating force that is used to regulate the interlocking movement member by the regulating portion, act on the first link and the second link in a direction away from the link coupling position when the first link and the second link form the substantially linear shape at the link coupling position, the toggle section being thereby configured to hold the substantially linear shape by the acting force, and configured to absorb a reaction force of the regulating force from the interlocking movement member.

3. The insertion apparatus according to claim 1,
   wherein the moving unit includes a slide member which is configured to move along the longitudinal axis between a first slide position when the moving unit is placed at the first movement position and a second slide position when the moving unit is placed at the second movement position, and
   the regulating portion includes an abutting member which is configured to move in a direction that is not parallel to the longitudinal axis when the slide member moves to the second slide position, and thereby configured to regulate movement of the interlocking movement member along the longitudinal axis when the abutting member abuts on the interlocking movement member.

4. The insertion apparatus according to claim 3,
   wherein the slide member includes a first inclined surface inclined with respect to the longitudinal axis, and
   the abutting member includes a second inclined surface which is provided to be parallel to the first inclined surface, and which is configured to move the abutting member in a direction perpendicular to the longitudinal axis when the slide member moves to the second slide position and the second inclined surface is pressed by the first inclined surface, the second inclined surface being thereby configured to bring the abutting member into contact with the interlocking movement member.

5. The insertion apparatus according to claim 1, further comprising a force amplifying unit which includes: a first member on which a first acting force acts by the switching operation to the state that the motion of the motion portion is regulated; and a second member on which a second acting force higher than the first acting force acts from the first member when the first acting force acts on the first member, the force amplifying unit being configured to amplify regulating force of regulating movement of the interlocking movement member.

6. The insertion apparatus according to claim 5,
wherein the first member is the first link or the second link, and
the first link or the second link serving as the first member is an L-shaped crank member which includes: a supporting point; a power point which is placed away from the supporting point by a first distance, and on which the first acting force acts; and a working point which is placed away from the supporting point by a second distance smaller than the first distance, and which allows the second acting force to act on the second member, the L-shaped crank member having the supporting point as an apex.

7. The insertion apparatus according to claim 5,
wherein the moving unit includes a slide member which is configured to move along the longitudinal axis between a first slide position when the moving unit is placed at the first movement position and a second slide position when the moving unit is placed at the second movement position,
the regulating portion includes an abutting member which is configured to move in a direction perpendicular to the longitudinal axis when the slide member moves to the second slide position, and configured to regulate movement of the interlocking movement member along the longitudinal axis when the abutting member abuts on the interlocking movement member,
the first member is the slide member,
the second member is the abutting member,
the slide member serving as the first member includes a first inclined surface inclined with respect to the longitudinal axis, and
the abutting member serving as the second member includes a second inclined surface which is provided to be parallel to the first inclined surface, the second inclined surface being configured to move the abutting member in the direction perpendicular to the longitudinal axis when the slide member moves to the second slide position by the first acting force and the second acting force acts from the first inclined surface.

8. The insertion apparatus according to claim 7,
wherein each of a first sharp angle between the first inclined surface and the longitudinal axis and a second sharp angle between the second inclined surface and the longitudinal axis is smaller than 45°.

9. The insertion apparatus according to claim 1,
wherein the transmitting portion includes a linear member which is extended in the insertion section along the longitudinal axis, and which is configured to be pulled in response to input of the operation,
the insertion section includes a first bending section configured to perform a bending motion when the linear member is pulled,
the motion portion includes a second bending section which is provided at a part of the insertion section to the proximal direction side of the first bending section, and which is configured to perform a bending motion in accordance with the bending motion of the first bending section, and
the interlocking movement member is configured to move along the longitudinal axis in tandem with the bending motion of the second bending section, and configured to fix and hold the second bending section when its movement is regulated by the regulating portion.

10. The insertion apparatus according to claim 9,
wherein the interlocking movement member is a bending fixing wire which is extended from an inside of the holding section to an inside of the insertion section along the longitudinal axis, and which has a distal end connected to a distal end portion of the second bending section, and
the regulating portion, to which a proximal end of the bending fixing wire is connected, is configured to pull the bending fixing wire toward the proximal direction when it moves in the proximal direction, and thereby the regulating portion is configured to fix and hold the second bending section when it holds the bending fixing wire in a tensed state.

11. The insertion apparatus according to claim 1, further comprising a stopper member on which the link unit is configured to abut at the link coupling position when the link unit has changed from a state that the substantially V-like shape having a first angle smaller than 180° and a second angle larger than 180° is formed at the link coupling position to a state that the substantially linear shape is formed at the link coupling position, the stopper member being thereby configured to avoid a change of the link unit to a state that an inverted V-like shape having the first angle larger than 180° and the second angle smaller than 180° is formed at the link coupling position, and configured to hold the link unit in the state that the substantially linear shape is formed at the link coupling position.

12. The insertion apparatus according to claim 11,
wherein, in the link unit in the state that the substantially linear state is formed, the first angle is larger than 180° and smaller than 185°, and the second angle is larger than 175° and smaller than 180°.

* * * * *